(12) United States Patent
Chen

(10) Patent No.: US 6,787,342 B2
(45) Date of Patent: Sep. 7, 2004

(54) PASTE FORMULATIONS

(75) Inventor: Jun Chen, Robbinsville, NJ (US)

(73) Assignee: Merial Limited, Iselin, NJ (US)

( * ) Notice: Subject to any disclaimer, the term of this patent is extended or adjusted under 35 U.S.C. 154(b) by 293 days.

(21) Appl. No.: 09/504,741

(22) Filed: Feb. 16, 2000

(65) Prior Publication Data

US 2003/0007958 A1 Jan. 9, 2003

(51) Int. Cl.$^7$ .............................. C12N 9/99; C12N 9/00; A61K 9/00
(52) U.S. Cl. ........................ 435/184; 435/183; 435/424; 435/400
(58) Field of Search ........................................ 424/94.1

(56) References Cited

U.S. PATENT DOCUMENTS

| | | | |
|---|---|---|---|
| 3,746,490 A | 7/1973 | Marsland et al. | |
| 4,605,563 A | 8/1986 | Heine et al. | |
| 4,891,211 A | 1/1990 | Winston | |
| 5,122,377 A | 6/1992 | Miller et al. | |
| 5,266,304 A | * 11/1993 | Baffelli et al. | ................. 424/49 |
| 5,698,584 A | * 12/1997 | Black et al. | ................. 514/462 |
| 5,708,017 A | 1/1998 | Dave et al. | |
| 5,880,076 A | * 3/1999 | Vermeer | ...................... 510/123 |
| 5,958,458 A | * 9/1999 | Norling et al. | ............. 424/490 |
| 5,981,576 A | * 11/1999 | Belley et al. | ................ 514/473 |
| 6,017,520 A | * 1/2000 | Synodis et al. | .......... 424/78.02 |
| 6,020,343 A | * 2/2000 | Belley et al. | ................ 514/309 |

FOREIGN PATENT DOCUMENTS

| | | |
|---|---|---|
| EP | 0 181 525 | 5/1986 |
| WO | WO 00/56346 | 9/2000 |

\* cited by examiner

*Primary Examiner*—Michael V. Meller
(74) *Attorney, Agent, or Firm*—Frommer Lawrence & Haug; Thomas J. Kowalski; Mark Russell

(57) ABSTRACT

This invention provides for a pharmaceutical or veterinary paste formulation comprising: an effective amount of a therapeutic agent; fumed silica; a viscosity modifier; a hydrophilic carrier; optionally, an absorbent; and optionally, a colorant, stabilizer, surfactant, or preservative. This invention also provides for methods of using these formulations for treating various disease states as well.

9 Claims, 14 Drawing Sheets needle-like particles big faceted crystals

PASTE FORMULATIONS

RELATED APPLICATIONS

Reference is made to the following U.S. applications: Ser. No. 09/346,905, filed Jul. 2, 1999, now allowed (U.S. Pat. No. 6,239,112); Ser. No. 09/112,690, filed Jul. 9, 1999, now allowed (U.S. Pat. No. 5,958,888); and Ser. No. 09/152,775, filed Sep. 14, 1998, now allowed (U.S. Pat. No. 6,174,540), entitled LONG ACTING INJECTIBLE FORMULATIONS CONTAINING HYDROGENATED CASTOR OIL. Reference is also made to EP 99 402 482.6, filed on Oct. 8, 1999. The disclosure of these patent applications as well as the references cited therein and the references cited herein are expressly incorporated by reference.

FIELD OF THE INVENTION

This invention provides for improved paste formulations suitable for pharmaceutical and veterinary use as well as methods for treating various disease states using these formulations. This invention also provides for an improved method for manufacturing paste formulations.

BACKGROUND OF THE INVENTION

Therapeutic agents are administered to animals and humans by a variety of routes. These routes include, for example, oral ingestion, topical application or parental administration. The particular route selected by the practitioner depends upon factors such as the physiochemical properties of the therapeutic agent, the condition of the host, and economics.

One method of formulating a therapeutic agent for oral, topical, dermal or subdermal administration is to formulate the therapeutic agent as a paste. Pastes have the advantage of being relatively easy to use. The disadvantage associated with their use is that often these products typically do not retain good chemical and physical stability over the shelf-life of the product. Hence, there is a need for improved paste formulations which do not exhibit the these undesirable properties.

One of the causes of these disadvantages is the inclusion of fumed silica as a viscosity agent. Fumed silica is commercially available and sold, for example, under the trade names of CAB-O-SIL (Cabot, TD11) and AEROSIL (Degussa, Technical Bulletin Pigments, No. 11 and No. 49). Fumed silica is an extremely light material (density 0.04 g/ml), which makes its handling and processing difficult. Moreover, because of its light density, fumed silica, when mixed with a vehicle, introduces a significant amount of air into the product. This occurs even at the relatively small amounts (6 to 8%) typically used to make pastes (6 to 8%). Unless the paste is processed under vacuum or a deareation step is added at the end of the process, it is not possible to remove such large amounts of air bubbles from the paste.

Figure 1:
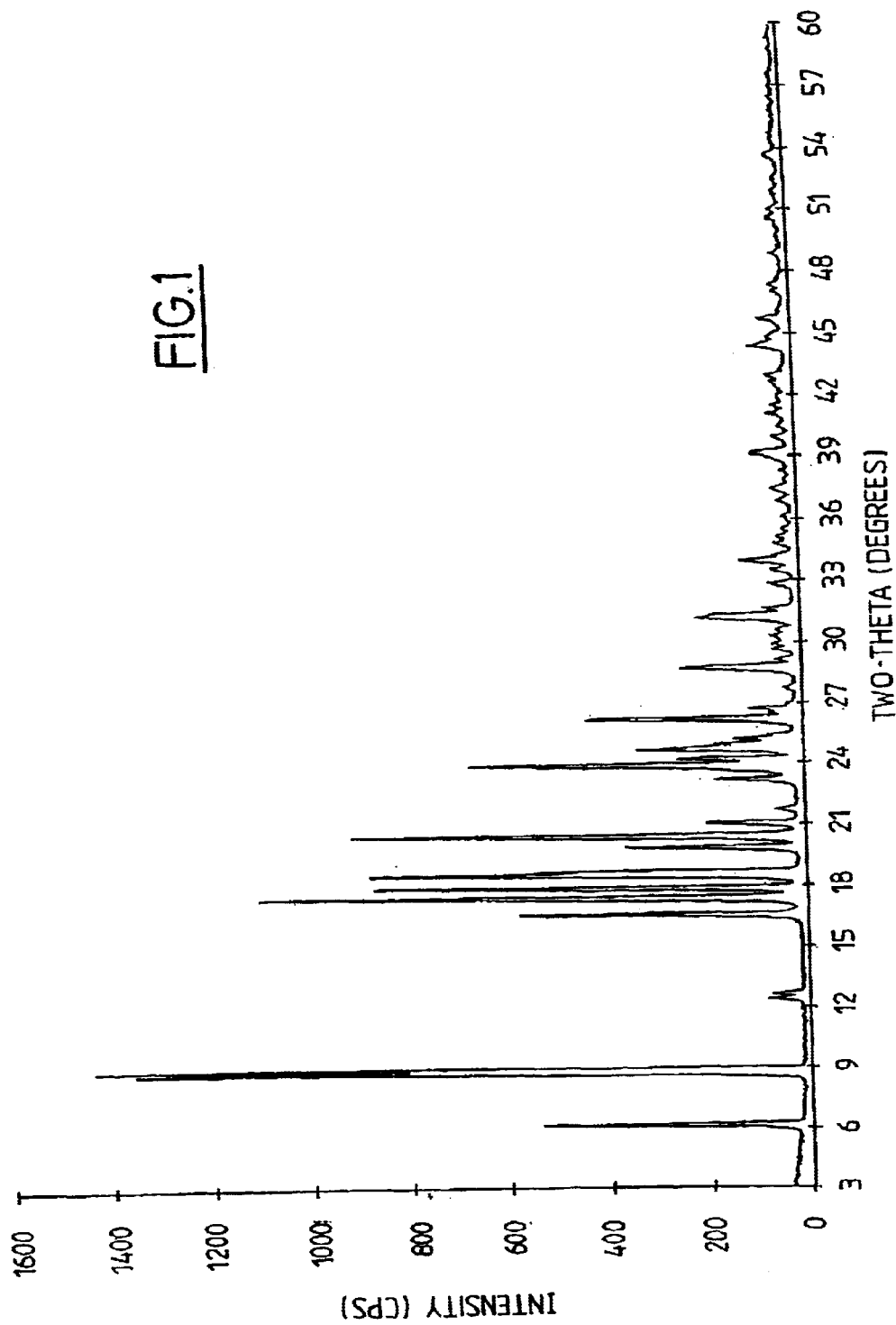
FIG. 1 depicts the change of viscosity as a function of increased CAB-O-SIL content wherein no viscosity modifier was added.

In order to demonstrate the problems associated with using fumed silica such as CAB-O-SIL, the viscosity of a paste as a function of CAB-O-SIL content was measured. FIG. 1 depicts the change of viscosity of the paste where no viscosity modifier was added. Triacetin was used as the vehicle in this study. When the CAB-O-SIT content was less than 5%, the paste remained thin as a free flow liquid and entrapped air could easily escape. After 5%, the viscosity increased dramatically and the additional air brought into the paste by the CAB-O-SIL could not escape and stayed in the paste. When about 7% of CAB-O-SIL was added, the paste had a penetration value of 35 mm. This amount is comparable with the initial penetration value of other commercially known pastes such as GASTROGARD (20–40 mm). Hence, in the absence of a viscosity modifier, at least 7% of CAB-O-SIL was needed to make pastes with useful viscosity. Because of the low density of CAB-O-SIL (0.04 g/ml), the amount of entrapped air is significant. Thus, unless processing under vacuum or adding a deareation step at the end, it is impossible to remove such large amounts of air in the paste and cannot control the accuracy of the dose.

Viscosity modifiers include compounds that have two or more functional groups which are capable of forming hydrogen bonds with the silanols on the surface of the fumed silica particles. Compounds which function as viscosity modifier include, for example, the polyethylene glycols ("PEGs"). These compounds are liquid and solid polymers which correspond to the general formula $H(OCH_2CH_2)_nOH$, where n is greater than or equal to 4, and are described in "The Merck Index", $10^{th}$ ed., M. Windholz and S. Budavari eds., p. 1092, Merck & Co., Inc., Rahway, N.J. (1983).

While not wishing to be bound by theory, in order to understand the mechanism of the viscosity modifiers, it is necessary to understand how CAB-O-SIL thickens a formulation. The hydrogen bonds between the silanol groups on the surface of the CAB-O-SIL particles are responsible for its thickening effect. CAB-O-SIL particles are connected through these hydrogen bonds to form a three-dimension network. The viscosity modifiers have two or more functional groups (e.g., —OH or —NH$_2$). These groups form hydrogen bonds with the silanols on the surface of CAB-O-SIL particles. These viscosity modifiers act as crosslinkers to extend the network structure and also increase the crosslinking density. This is why the addition of a small amount of the viscosity modifiers dramatically increased the viscosity of the pastes.

Figure 2:
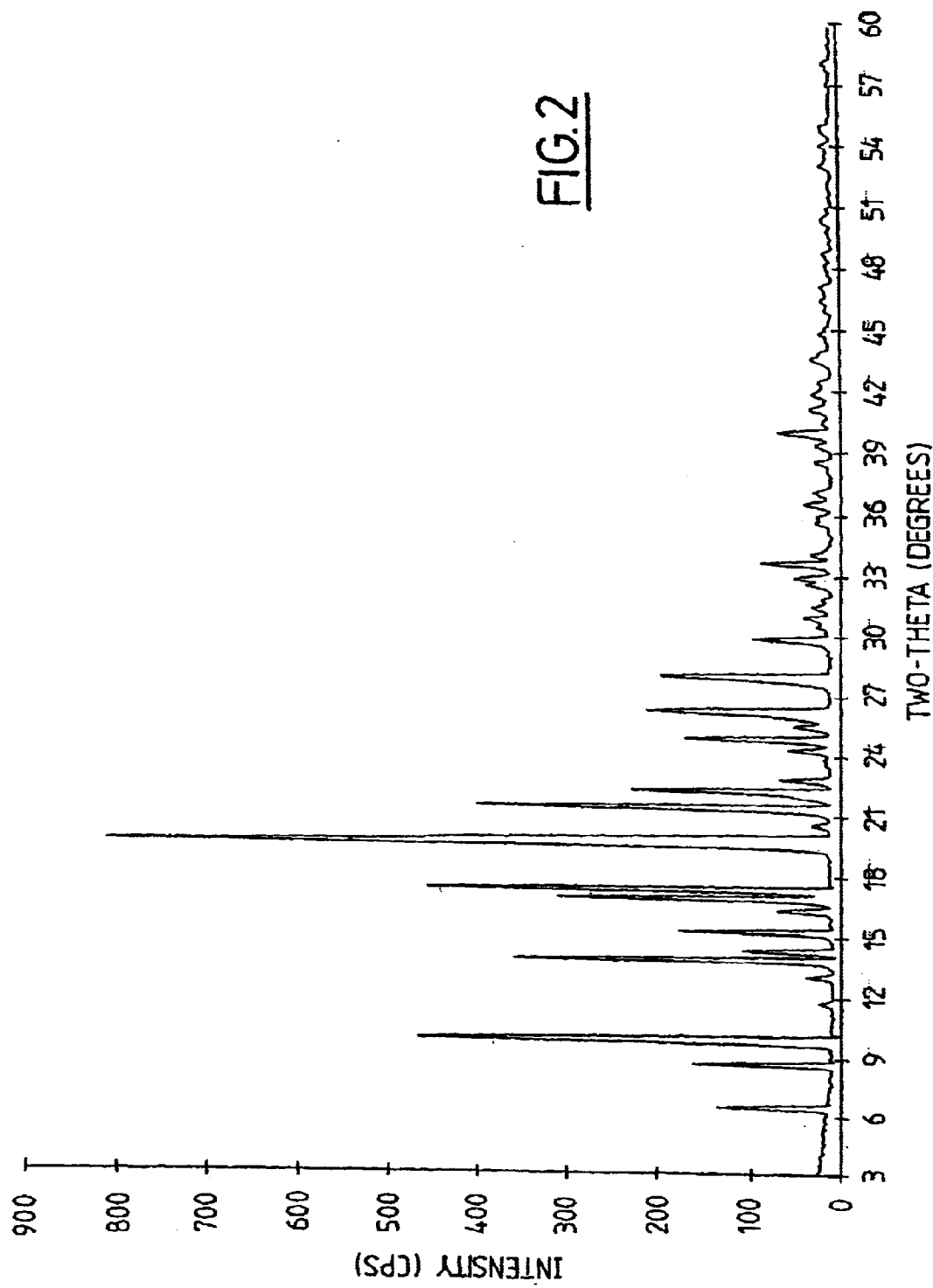
FIG. 2 depicts the impact of the viscosity modifier, PEG 300, on the paste viscosity of initial and after storage for 6 days at 60° C.

In order to demonstrate this, placebo pastes containing 4% CAB-O-SIL and 0.1–3.0% polyethylene glycol ("PEG") 300 in triacetin were prepared and their viscosity values were measured using penetrometer (FIG. 2). Before the addition of PEG 300, the viscosity was too low to be tested on penetrometer (>65 mm). The viscosity jumped dramatically with just the addition of only 0.1% PEG 300. The viscosity increased further when more PEG 300 was added. After the PEG level reached 0.5%, the viscosity increase plateaued. From 0.5–3.0%, the viscosity remained about the same, although a slight decrease in viscosity was seen when more than 2% PEG was added.

Figure 3:
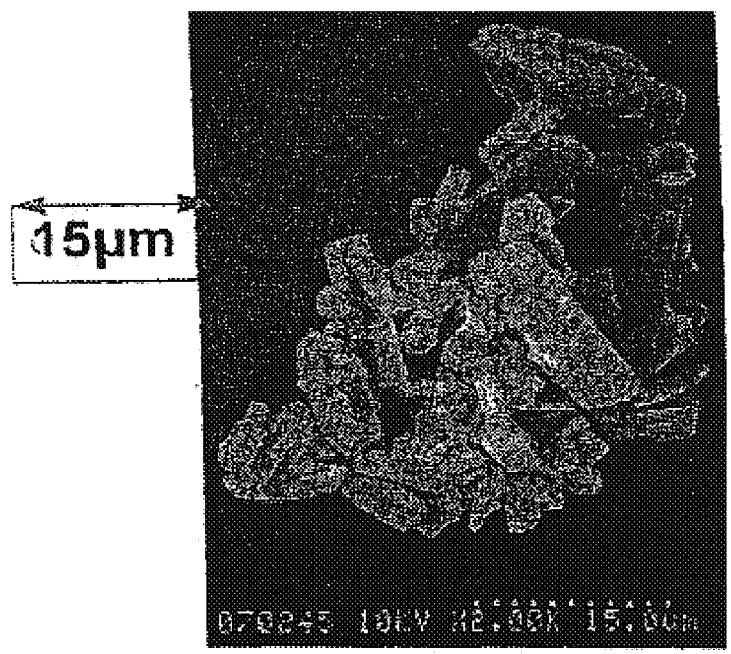
FIG. 3 depicts the schematic representation of the competition of excess PEG molecules with the crosslinking PEG molecules.

FIG. 3 depicts what is believed to be happening at the molecular level. FIG. 3 depicts the competition of excess PEG molecules with the crosslinking PEG molecules at the molecular level. The figure indicates that the silanol groups on the surface of CAB-O-SIL particles were saturated when more than 0.5% PEG was added. The extra PEG molecules could no longer increase the viscosity because it could not find two free silanol groups on two different particles to increase further the viscosity. On the contrary, the free PEG molecules actually compete with the bonded PEG molecules that crosslinks two particles (FIG. 3). As a result, some of the crosslinks dissociate and the viscosity decreases slightly. Based on FIG. 2, the ideal range of PEG 300 is about 0.2% to about 1.5% for this particular paste.

Thus, as depicted in FIG. 1, the prior pastes use a relatively high amount of fumed silica to achieve the proper viscosity. The effect of this is that a large amount of air will be entrapped into the paste, which causes, for example, dose inaccuracy, shrinkage, liquid separation (whipping) and discoloration of the paste. Further, the therapeutic agent may also oxidize. Moreover, when a large amount of fumed silica is used in an oral paste, the paste imparts a sandy feel to the mouth. This sandy feel causes the product less palatable. Furthermore, the manufacturing costs to prepare the pastes are expensive because the process must occur under vacuum or a subsequent deareation step at the end of the process is required. Additional manufacturing costs are incurred because fumed silica is relatively expensive and very difficult to handle due to its extremely low density. The present invention overcomes these as well as other disadvantages.

SUMMARY OF THE INVENTION

The present invention provides for a stable paste formulation for a wide range of veterinary and pharmaceutical products. The present invention also provides for an improved process to make the inventive paste products. The formulations of the present invention exhibit good chemical and physical stability over the shelf life and maintain the chemical integrity, texture, consistency and viscosity over a wide temperature range. The inventive manufacturing process provides for a simple, fast and economical process for preparing the inventive paste formulations that avoids heating and cooling during manufacturing and entrapment of air, a common problem in the manufacturing of paste dosage forms.

These and other embodiments are disclosed or are obvious, from and encompassed by, the following Detailed Description.

DETAILED DESCRIPTION

The present invention provides for a pharmaceutical or veterinary paste formulation comprising:

(a) an effective amount of a therapeutic agent;

(b) fumed silica;

(c) a viscosity modifier;

(d) a carrier;

(e) optionally, an absorbent; and (f) optionally, a colorant, stabilizer, surfactant, or preservative.

This invention also provides for a process for preparing a paste formulation comprising the steps of:

(a) dissolving or dispersing the therapeutic agent into the carrier by mixing;

(b) adding the fumed silica to the carrier containing the dissolved therapeutic agent and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The steps are illustrating, but not limiting. For Example, step (a) can be moved to the last step.

More preferred are pharmaceutical and veterinary pastes comprising:

(a) a therapeutic agent selected from the group consisting of insecticides, acaricides, parasiticides, growth enhancers, oil-soluble NSAIDS or a proton pump inhibitor;

(b) fumed silica;

(c) a viscosity modifier;

(d) an absorbent;

(e) a colorant; and (f) a carrier which is triacetin, a monoglyceride, a diglyceride, or a triglyceride.

Also preferred are pastes comprising:

(a) a therapeutic agent selected from the group consisting of avermectins, milbemycins, nordulisporic acid and its derivatives, estrogens, progestins, androgens, substituted pyridyl methyl derivatives, phenylpyrazoles, COX-2 inhibitors or 2-(2-benzimidazolyl)-pyrimidine derivatives;

(b) fumed silica;

(c) a viscosity modifier;

(d) an absorbent;

(e) a colorant; and (f) a hydrophilic carrier which is triacetin, a monoglyceride, a diglyceride, or a triglyceride.

The above compositions wherein the viscosity modifier is PEG 200, PEG 300, PEG 400, PEG 600, monoethanolamine, triethanolamine, glycerol, propylene glycol, polyoxyethylene (20) sorbitan mono-oleate (polysorbate 80 or Tween 80), polyoxamers (e.g., Pluronic L 81); the absorbent is magnesium carbonate, calcium carbonate, starch, or cellulose and its derivatives; and the colorant is titanium dioxide iron oxide, or FD&C Blue #1 Aluminum Lake are most especially preferred.

The therapeutic agents which are used in the inventive formulations are those which are known to the practitioner as agents which may be formulated as pastes. Classes of therapeutic agents contemplated by the inventive formulations include insecticides, acaricides, parasiticides, growth enhancers, oil-soluble, nonsteroidal anti-inflammatory drugs (NSAIDS), proton pump inhibitors and antibacterial compounds. Specific classes of compounds which fall within these classes include, for example, avermectins, milbemycins, nodulisporic acid and its derivatives, estrogens, progestins, androgens, substituted pyridylmethyl derivatives, phenylpyrazoles, COX-2 inhibitors, 2-(2-benzimidazolyl)-pyrimidines derivatives and macrolide antibiotics.

The avermectin and milbemycin series of compounds are potent anthelmintic and antiparasitic agents against a wide range of internal and external parasites. The compounds which belong to this series are either natural products or are semi-synthetic derivatives thereof. The structure of these two series of compounds are closely related and they both share a complex 16-membered macrocyclic lactone ring; however, the milbemycin do not contain the aglycone substituent in the 13-position of the lactone ring. The natural product avermectins are disclosed in U.S. Pat. No. 4,310,519 to Albers-Schonberg, et al., and the 22, 23-dihydro avermectin compounds are disclosed in Chabala, et at., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycin are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, and U.S. Pat. No. 4,920,148.

Avermectins and milbemycins share the same common 16-membered macrocyclic lactone ring; however, milbemycins do not possess the disaccharide substituent on the 13-position of the lactone ring.

While many avermectin compounds are known in the art, a representative structure of the class of compounds is as follows:

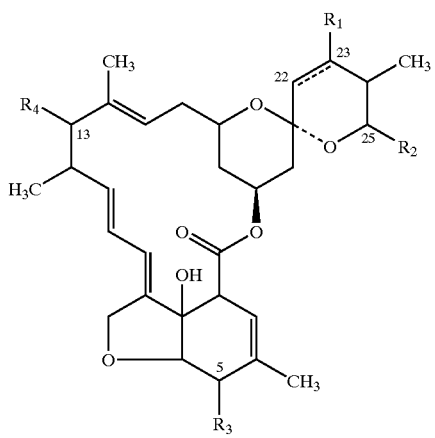

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl; and $R_4$ is hydrogen, hydroxy or

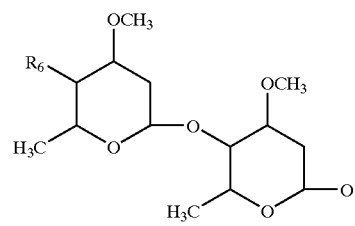

where $R_6$ is hydroxy, amino, mono-or di-lower alkylamino or lower alkanoylamino.

The preferred compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad spectrum antiparasitic agents. The structures of abamectin and ivermectin are as follows:

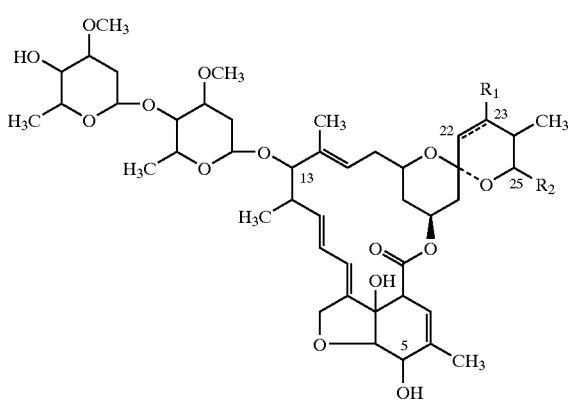

wherein for abamectin the broken line represents a double bond and $R_1$ is not present and for ivermectin the double bond represents a single bond and $R_1$ is hydrogen; and $R_2$ is isopropyl or sec-butyl.

The 4"-acetyl amino-5-ketoximino derivatives of avermectin B1aB1b has the following structural formula:

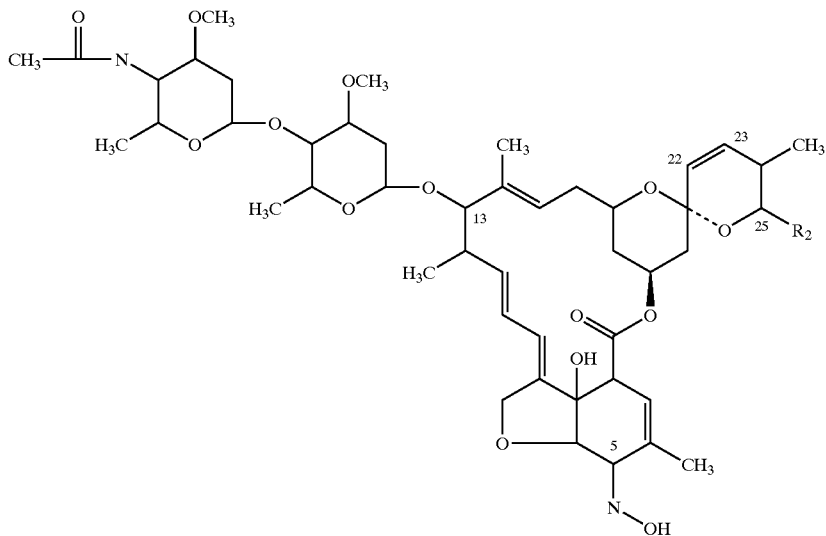

where R₂ is isopropyl or sec-butyl.

The avermectin products are generally prepared as a mixture of at least 80% of the compound where R₂ is sec-butyl and no more than 20% of the compound where R₂ is isopropyl.

Other preferred avermectins, include ememectin, epinomectin and doramectin. Doramectin is disclosed in U.S. Pat. No. 5,089,490 and EP 214 738. This compound has the following structure:

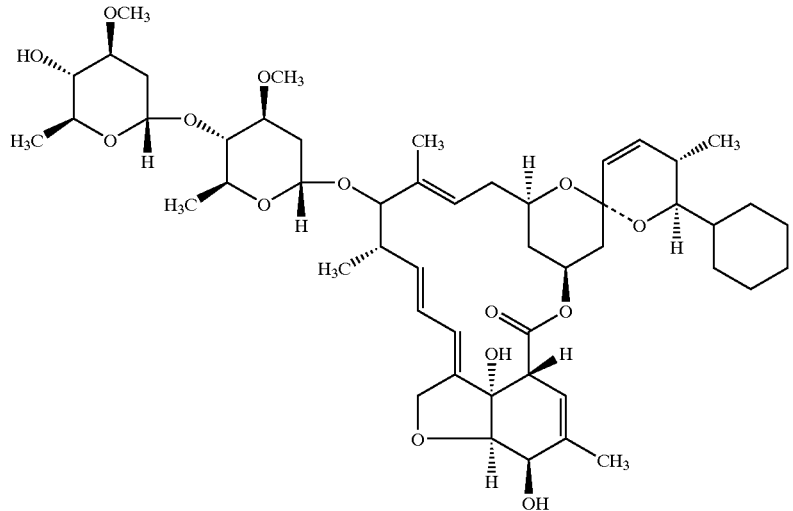

In the present formulations, ivermectin is especially preferred.

A representative structure for a milbemycin is that for milbemycin $\alpha_1$:

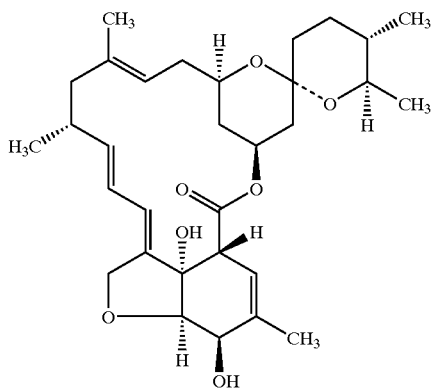

An especially preferred milbemycin is moxidectin, whose structure is as follows:

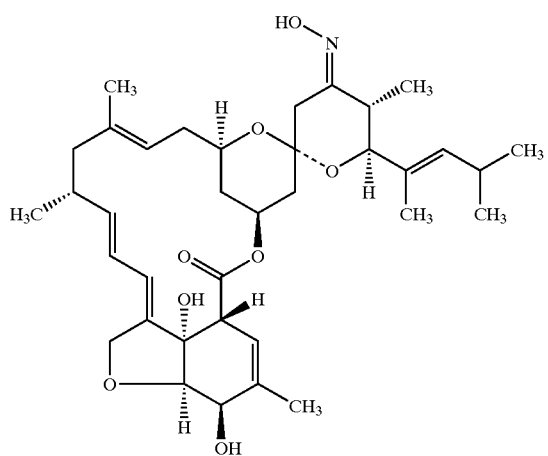

The compound is disclosed in U.S. Pat. No. 5,089,490.

The monosaccharide avermectin derivatives are also preferred especially where an oxime substitution is present on the 5-position of the lactone ring. Such compounds are described, for example, in EP 667,054. Selamectin is an especially preferred compound of this class of derivatives.

Nodulisporic acid and its derivatives are a class of acaricidal, antiparasitic, insecticidal and anthelmintic agents well known to a practitioner of the art. These compounds are used to treat or prevent infections in humans and animals. These compounds are described, for example, in U.S. Pat. No. 5,399,582 and WO 96/29073. Additionally, the compounds can be administered in combination with other insecticides, parasiticides, and acaricides. Such combinations include anthelmintic agents, such as those discussed above which include ivermectin, avermectin, and emamectin, as well as other agents such as thiabendazole, febantel or morantel; phenylpyrazoles such as fipronil; and insect growth regulators such as lufenuron. Such combinations are also contemplated in the present invention.

Generally, all classes of insecticides are provided for in this invention. One example of this class include substituted pyridylmethyl derivatives such as imidacloprid. Agents of this class are described, for example, in U.S. Pat. No. 4,742,060 or in EP 892,060. It would be well within the skill level of the practitioner to decide which individual compound can be used in the inventive formulation to treat a particular infection of an insect.

Phenylpyrazoles are another class of insecticides which possess excellent insecticidal activity against all insect pests including blood-sucking pests such as ticks, fleas etc., which are parasites on animals. This class of agents kills insects by acting on the gamma-butyric acid receptor of invertebrates. Such agents are described, for example, in U.S. Pat. No. 5,567,429, U.S. Pat. No. 5,122,530, and EP 295,117. An especially preferred phenylpyrazole is fipronil, whose chemical name is 5-amino-3-cyano-1-(2,6-dichloro-4-trifluoromethylphenyl)-4-trifluoromethylpyrazole. Fipronil is well known in the art as a flea and tick agent. It would be well within the skill level of the practitioner to decide which individual compounds can be used in the inventive formulations.

Insect growth regulators are another class of insecticides or acaricides, which are also provided for in the inventive formulations. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; and U.S. Pat. No. 4,751,225, as well as in EP 179,022 or U.K. 2,140,010. Especially preferred insect growth regulators include diflubenzuron, lufenuron, methoprene, phenoxycarb, pyriproxyfen, and cyromazine. Again, it would be well within the skill level of the practitioner to decide which individual compounds can be used in the inventive formulation.

Estrogens, progestins, and androgens refers to classes of chemical compounds which are also well known to a practitioner in this art and used, for example, to regulate fertility in humans and animals. In fact, estrogens and progestins are among the most widely prescribed drugs and are used, for example, alone or in combination for contraception or hormone replacement therapy in post menopausal women. Estrogens and progestins occur naturally or are prepared synthetically. This class of compounds also includes estrogens or progesterone receptor antagonists. Antiestrogens, such as tamoxifen and clomiphene, are used to treat breast cancer and infertility. Antiprogestives are used as contraceptives and anticancer drugs, as well as to induce labor or terminate a pregnancy.

The androgens and antiandrogens structurally related to the estrogens and progestins as they are also biosynthesized from cholesterol. These compounds are based on testosterone. Androgens are used for hypogonadism and promote muscle development. Antiandrogens are used, for example, in the management of hyperplasia and carcinoma of the prostate, acne, and male pattern baldness as well as in the inhibition of the sex drive in men who are sex offenders. Estrogen, progestins, and androgens are described, for example, in "Goodman & Gilman's The Pharmacological Basis of Therapeutics," $9^{th}$ ed., J. G. Handman and L. Elimbird, eds., Ch. 57 to 60, pp. 1411–1485, McGraw Hill, N.Y. (1996) or in "Principles of Medicinal Chemistry," $2^{nd}$ ed., W. O. Foye, ed., Ch. 21, pp. 495–559, Lea & Febiger, Philadelphia (1981).

Estrogens, progestins and androgens are also used in animal husbandry as growth promoters for food animals. It is known in the art that compounds of these classes act as growth-promoting steroids in animals such as cattle, sheep, pigs, fowl, rabbits, etc. Delivery systems to promote the growth of animals are described, for example, in U.S. Pat. No. 5,401,507, U.S. Pat. No. 5,288,469, U.S. Pat. No. 4,758,435, U.S. Pat. No. 4,686,092, U.S. Pat. No. 5,072,716 and U.S. Pat. No. 5,419,910.

Specific estrogen, progestin and androgen compounds are well known to the practitioner. Especially preferred compounds belonging to this class include progesterone, estradiol benzoate and trenbolone acetate.

NSAIDS are well known in the art. The classes of compounds which belong to this group include salicylic acid derivatives, para-aminophenol derivatives, indole and indene acetic acids, heteroaryl acetic acids, arylpropionic acids, anthranilic acids (fenamates), enolic acids, and alkanones. NSAIDS exert their activity by interfering with prostaglandin biosynthesis by irreversibly or reversibly inhibiting cyclooxygenase. Compounds of this group possess analgesic, antipyretic and nonsteroidal anti-inflammatory properties. Compounds belonging to these classes are described, for example, in Chapter 27 of Goodman and Gilman on pages 617 to 658 or in Ch. 22 of Foye on pages 561 to 590 as well as in U.S. Pat. No. 3,896,145; U.S. Pat. No. 3,337,570; U.S. Pat. No. 3,904,682; U.S. Pat. No. 4,009,197; U.S. Pat. No. 4,223,299; and U.S. Pat. No. 2,562,830, as well as the specific agents listed in The Merck Index. This invention contemplates those compounds that are oil-soluble.

Oil-soluble NSAIDS are also well known to the practitioner. Classes of NSAIDS which are preferred are indole and indecene acetic acids and heteroaryl acetic acids. Especially preferred compounds include indomethacin, ketorolac, caprofen, flunixin, ketoprofen, meloxicam, naproxen, and phenylbutazone.

COX-2 inhibitors are an especially preferred class of NSAIDS. As with other NSAIDS, COX-2 inhibitors are effective in treating cyclooxygenase mediated diseases such as inflammation, analgesia and fever. These compounds are especially effective in treating cancer, rheumatoid arthritis and osteoarthrilis. These compounds have the advantage of not affecting the integrity of the gastrointestinal tract and the renal blood flow. Examples of these compounds include (methylsulfonyl)phenyl-2-5(H)-furanone derivatives. These derivatives are described, for example, in copending application U.S. Ser. No. 09/097,537, now allowed, which in turn is a CIP of application U.S. Ser. No. 08/728,512, filed on Oct. 9, 1996, which in turn is based upon provisional applications Nos. 60/005,371 and 06/011,673. Especially preferred COX-2 inhibitors include 3-(cyclopropylmethoxy)-5,5-dimethyl-4-(4-methylsulfonyl) phenylyl)-5H-furan-2-one or 3-(cyclopropylethoxy)-5,5-dimethyl-4-(4-methylsulfonyl)phenyl)-5H-furan-2-one or pharmaceutically acceptable salts or hydrates of these compounds. An especially preferred COX-2 inhibitor is polymorphic form B of 3-(cyclopropylmethoxy)-4-[4-(methylsulfonyl)phenyl]-5,5-dimethyl-5H-furan-2-one. This compound is described in EP 99 402 482.6, which is incorporated herein by reference and discussed in general detail below.

An additonal embodiment of the present invention is a crystalline form of polymorph B with pharmaceutically acceptable bases, pharmaceutical compositions and methods of making and using polymorph B, preparing polymorphic B comprising agitating polymorphic Form A in the presence of methanol, a method for preparing polymorphic Form B comprising agitating polymorphic Form A in the presence of polymorphic Form B seeds in methanol.

WO 97/14691 discloses methylsulfonylphenyl-5H-furan-2-one compounds which are potent COX-2 inhibitors, namely 3-(cyclopropylmethoxy)-4-[4-(methylsulfonyl) phenyl]-5,5-dimethyl-5H-furan-2-one which was isolated in a crystalline form which is herein designated as "Polymorphic Form A or Polymorph A".

The formula of 3-(cyclopropylmethoxy)-4-[4-(methylsulfonyl)phenyl]-5,5-dimethyl-5H-furan-2-one is the following.

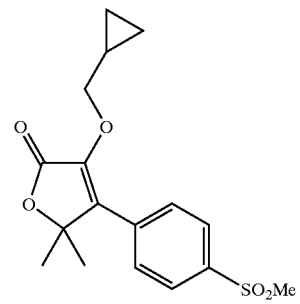

Recrystallization of polymorph A for purification purposes leaded to solubility problems in methyltertiobutylether.

Mixtures of 3-(cydopropylmethoxy)-4-(4-methylsulfonyl)phenyl-5,5-dimethylfuranone solid at 6.3% weight in methyltertiobutylether could no longer be solubilised. After dilution and recrystallization, the powder obtained was analysed by X-Ray diffraction and showed a different pattern than the initial product.

The experiment was reproduced in several solvents such as methanol and dimethylformamide. The new solid form obtained was named polymorph which is useful as a "non steroidal antiinflammatory agent" for the treatment of cyclooxygenase-2 mediated diseases.

Polymorph B possesses better flow characteristics than Polymorph A and is thermodynamically more stable than Polymorph A. Thus, Polymorph B is easier to handle (remove from vessel and transfer to filter), filter and dry than Polymorph A. Polymorph B is also easier to feed and micronize. Hence, the methods for its manufacture are more easily validated than that of Polymorph A.

Polymorph B may be characterized by its powder X-ray diffraction pattern hereinafter described in greater detail in FIGS. 6–16.

Powder X-ray Diffraction

The powder X-ray diffraction pattern of Polymorph A and Polymorph B was obtained by completely and uniformly filling the sample holder of the SIEMENS D5000 with the sample utilizing a spatula. The sample was then irradiated with the SIEMENS D5000 under the conditions described in Table 10.

TABLE 10

| Parameters for powder X-Ray Diffraction | |
|---|---|
| Instrument: | Siemens D5000 |
| X-Ray Target | Copper (d = 1.54 Å) |
| Voltage | 40 kV |
| Current | 30 mA |
| Detector | Scintillator |
| Two-theta range | 3°–60° |
| Scar Type | continuous |
| Chopper Increment | 0.01° |
| Beam Slit | 0.5° |
| Receiving beam scatter slit | 0.5° |

TABLE 10-continued

Parameters for powder X-Ray Diffraction

| Receiving detector slit | 6 mm |
|---|---|
| Atmosphere | Air |

Atmosphere Air

Figure 6:
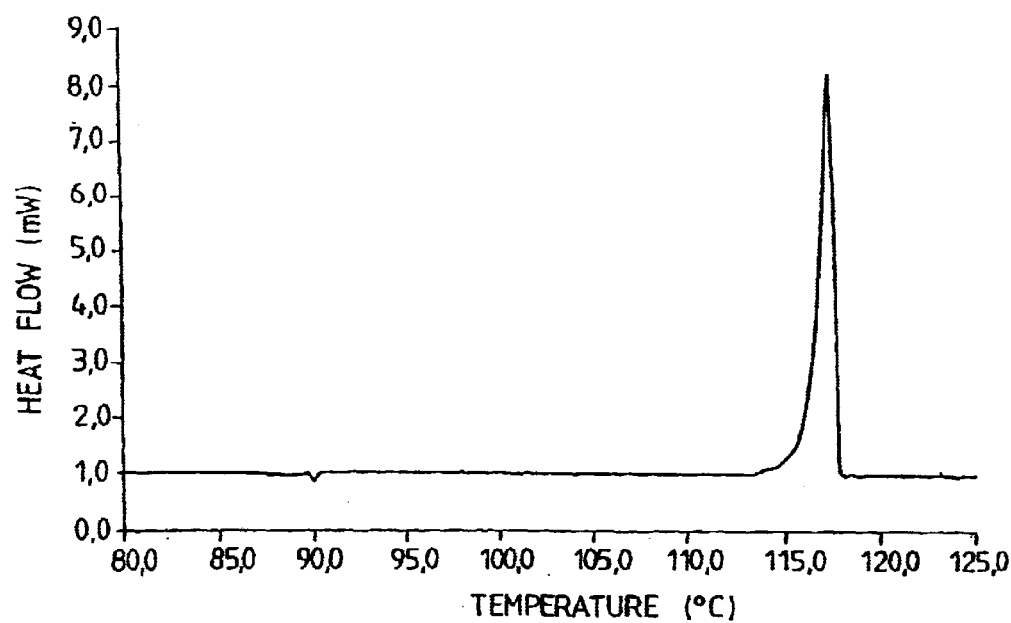
FIG. 6 depicts the XRPD pattern of form A.
Figure 7:
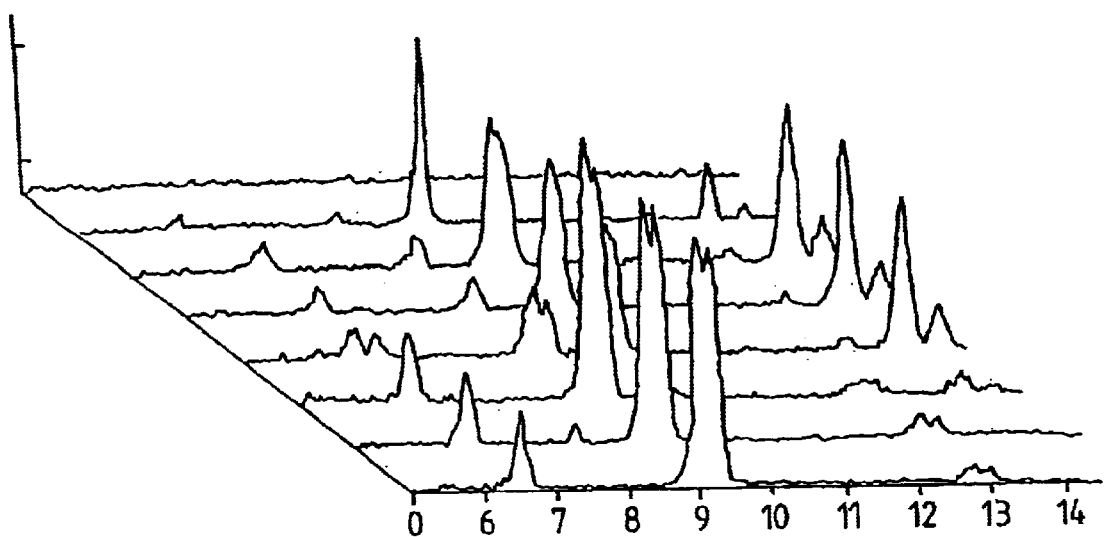
FIG. 7 depicts the XRPD pattern of form B.
Figure 8:
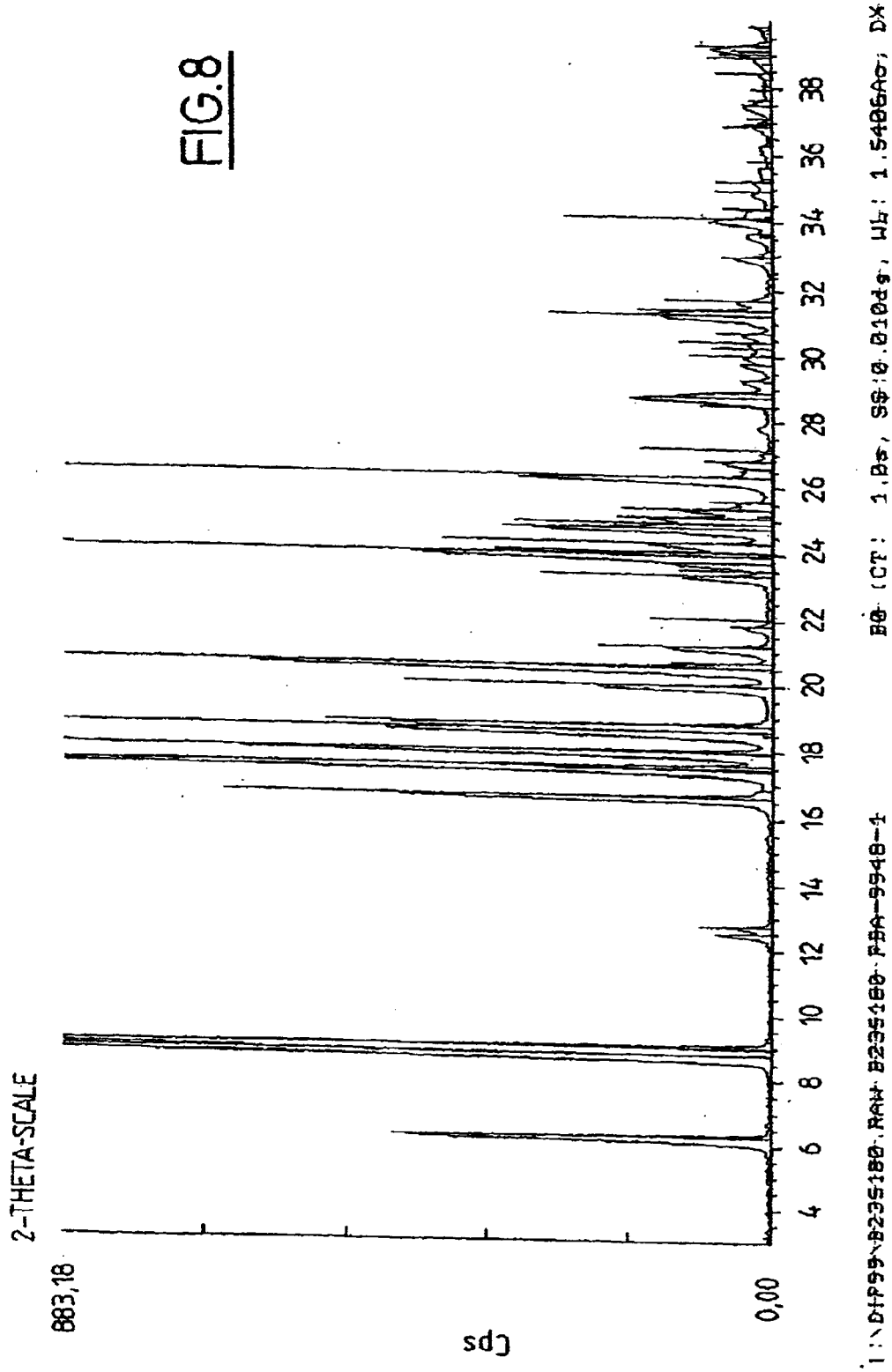
FIG. 8 depicts the habit pattern of form A.

The X-ray powder diffraction pattern of the micronized form of Polymorph A and B are represented respectively in FIGS. 6 and 7.

Handling Properties

It has been discovered that the new polymorphic form B had more advantageous handling properties in the micronization or preparation of pharmaceutical compositions.

After crystallization and before micronization, the Carr Index of B form is lower than 10 (in %). The Can Index CI is defined as $$CI = \frac{P-L}{P}$$

where P is the packed bulk density (g cm$^{-3}$), L is the loose bulk density (g cm 3). CI is also known as a compressibility index. A low figure for CI corresponds to a high degree of flowability.

The Carr Index way be calculated from Mercury Intrusion Porosimetry or measured by Tap-Tap.

Examples of Carr Index for unmilled products are given in table 11.

TABLE 11

| Polymorphic form | Crystallisation Process | Carr Index |
|---|---|---|
| A | Lab scale | 26 to 27 |
| A | Pilot scale | 29 to 33 |
| B | Recrystallisation in MTBE Lab scale | 2 to 3 |
| B | Recrystallisation in MTBE Pilot scale | 2 to 4 |

Figure 9:
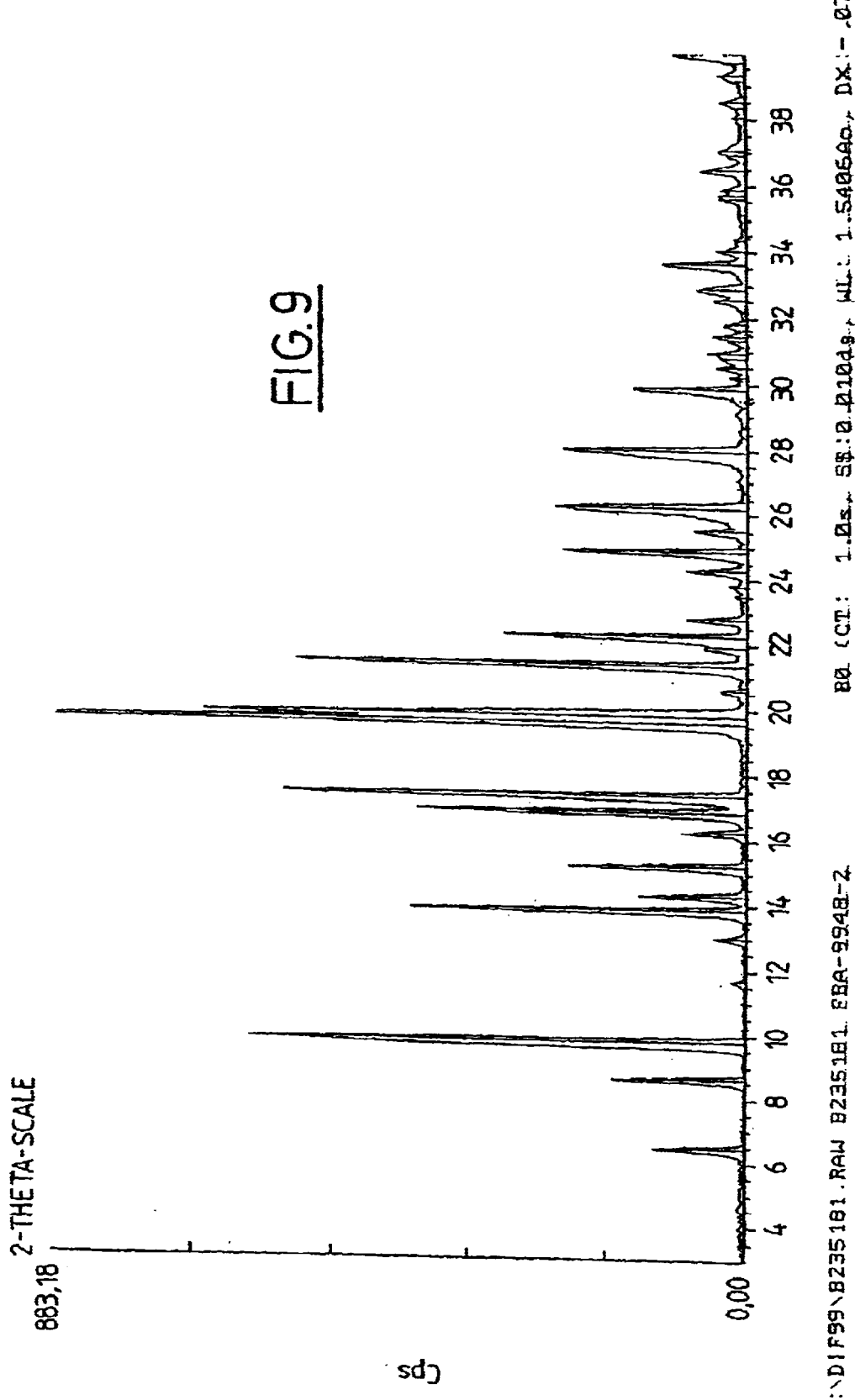
FIG. 9 depicts the habit pattern of form B.
Figure 10:
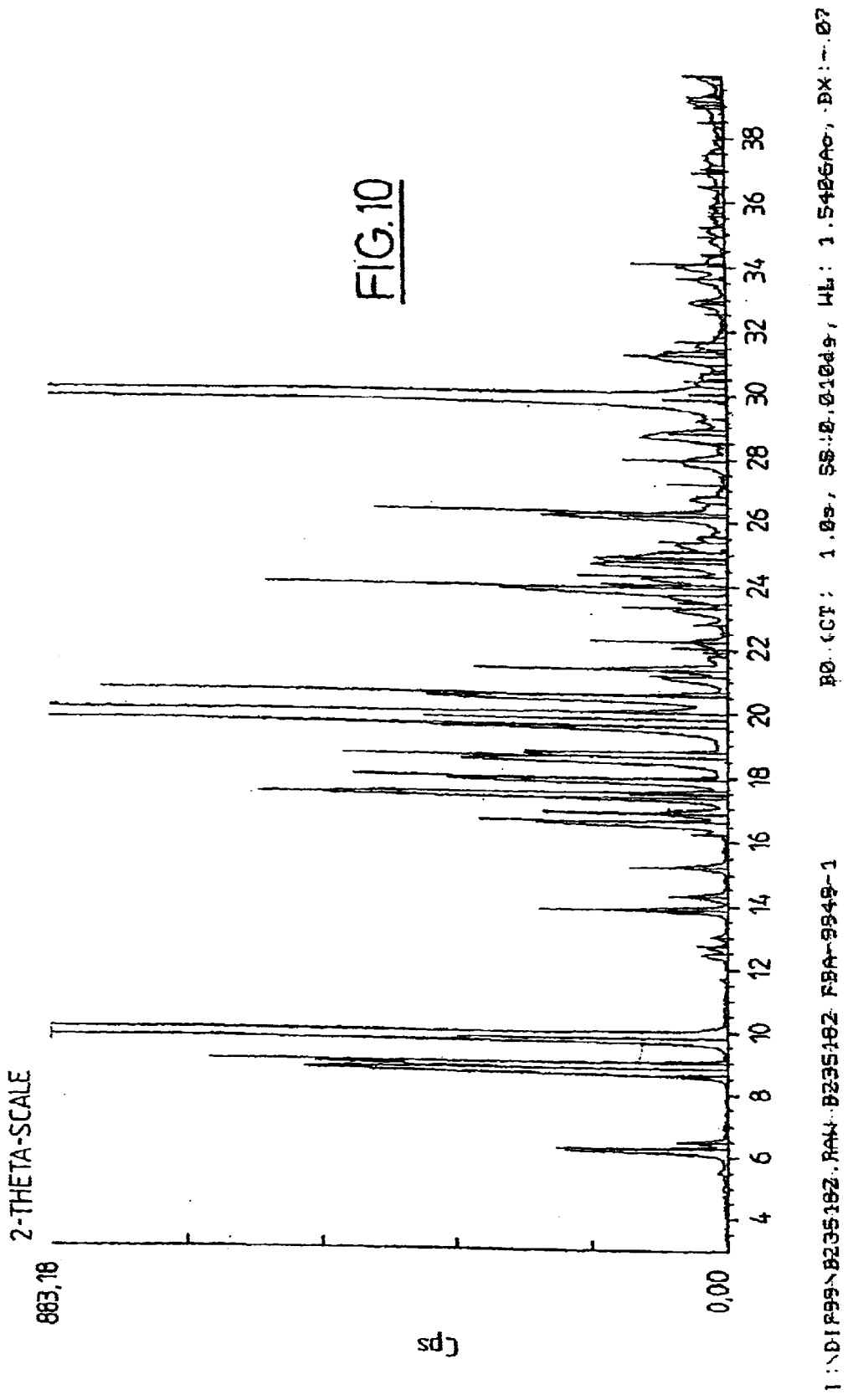
FIG. 10 depicts the DSC curve of a form A product heated at 4° C./mn.
Figure 11:
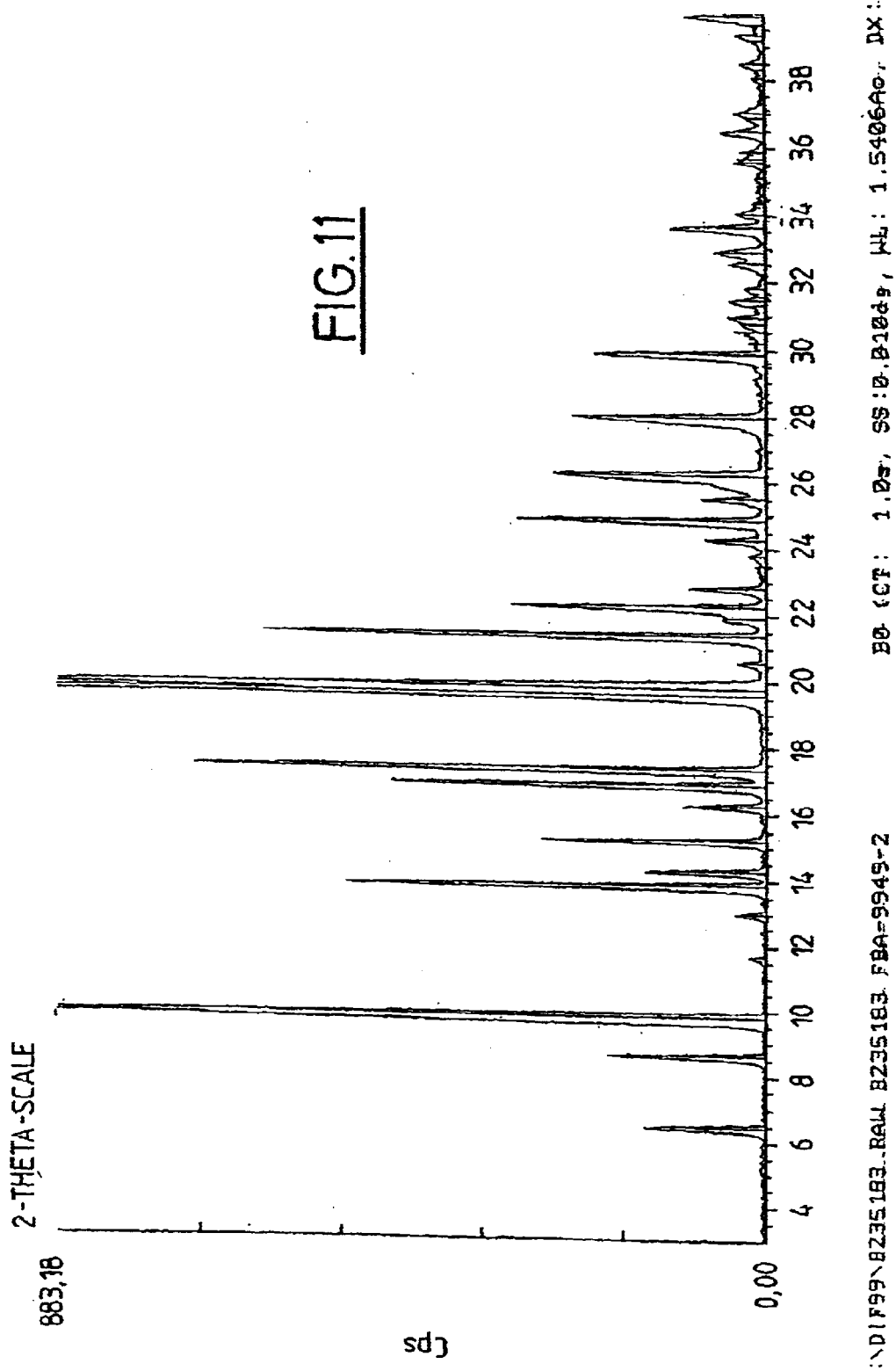
FIG. 11 depicts the DSC curve of a form A product heated at 2° C./mn.

These better handling properties are due to
  bigger crystals (before micronization),
  a more regular shape.
Form A is made of needle-like crystals (FIG. 8) when form B is mode of big faceted crystals (FIG. 9).

DSC (Differential Scanning Calorimetry)

When heated, form A transforms to form B depending on the heating rate.

Figure 12:
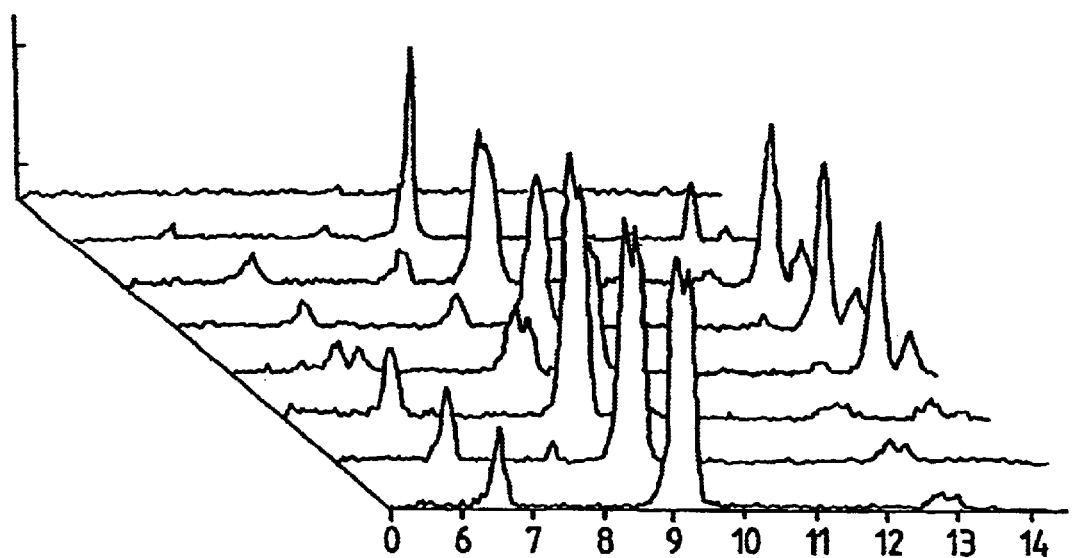
FIG. 12 shows the X-ray diffraction patterns at 30° C., −10°, 80, 90, 100, 110, 120 and 130° C. with form A at 30° C. and form B appearing at 80° C. At 130° C., there is no signal as all the product is melted.
Figure 13:
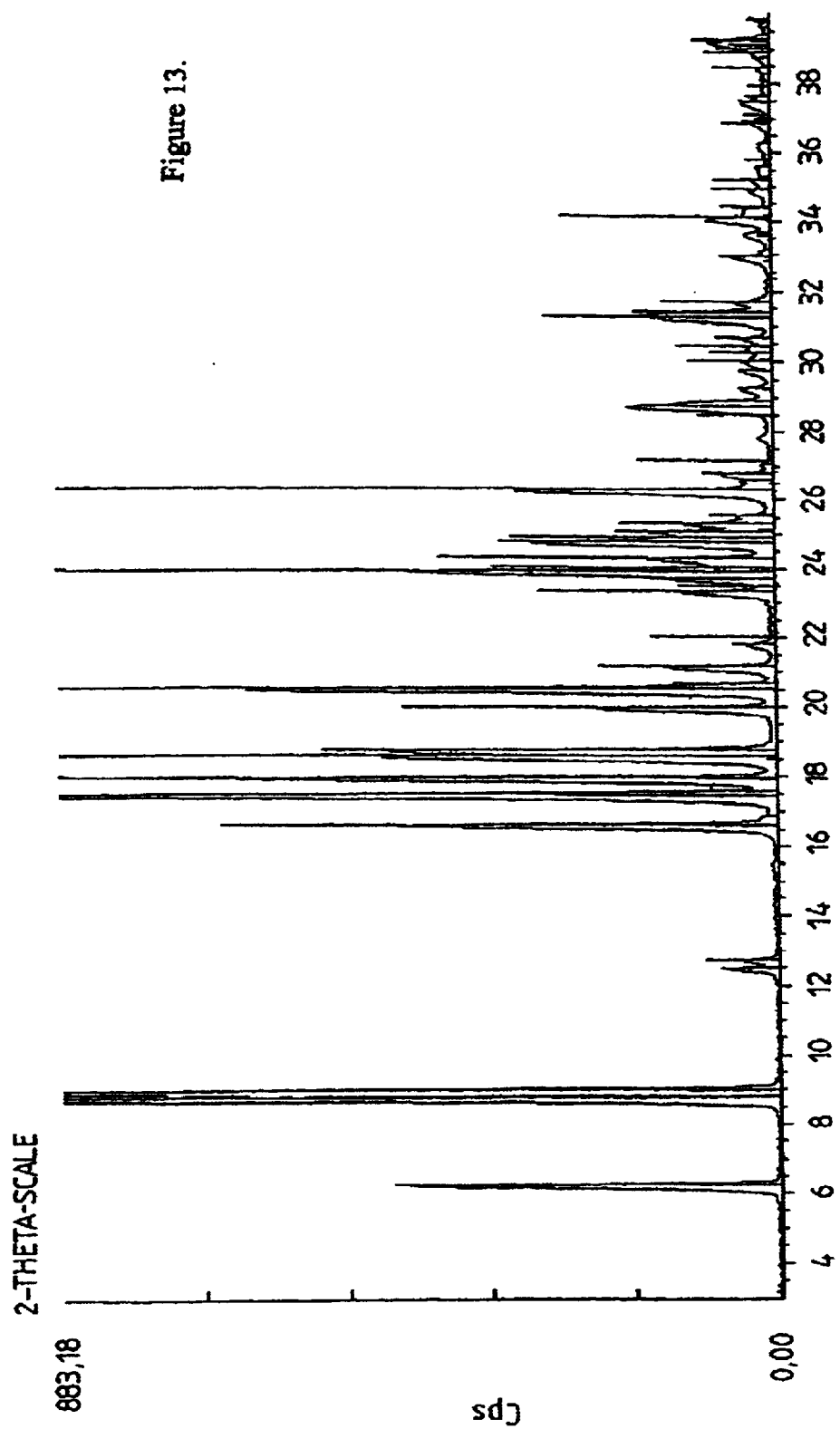
FIG. 13 represents the X-ray diffraction pattern of the initial reaction medium used for converting Polymorph A to polymorph B without seeding.

For instance, when the heating rate is 40° C./mn, the DSC curve shows (FIG. 10)
  an endothermal peak around 90–100° C. due to melting of A form,
  an exothermal peak corresponding to the transition A→B,
  an endothermal peak around 120° C. due to melting of B form,
when the heating rate is 2° C./mn (FIG. 11) the DSC curve shows:
  a very small exothermal peak corresponding to the transition A→B,
  an endothermal peak due to melting of B form.
Therefore, the transition A→B is under kinetic control as usual in case of polymorphism. The transition from A to B may also be followed by XRay under heating (FIG. 12).

According to Burger's rule ("On the Polymorphism of Pharmaceuticals an Other Molecular Crystals"—Theory of Thermodynamic Rules; A. BURGER—R; RAMBERGER—Mikrochimica Ada 1979; II, 259–271), the system is monotropic, and the B form is the most stable form.

The invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of Polymorph B.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of Polymorph B.

In another embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a human or animal in need of such treatment of a non-toxic therapeutically effective amount of a compound of 3-(cyclopropylmethoxy)-4-[4-(methylsulfonyl)phenyl]-5,5-dimethyl-5H-furan-2-one as disclosed herein.

The pharmaceutical compositions of the present invention comprise Polymorph B as an active ingredient, and may also contain a pharmaceutically acceptable carrier and optionally other therapeutic ingredients.

Polymorph B is useful for the relief of pain, fever and inflammation of a variety of conditions including signs associated with bacterial and viral infections, sprains and strains, tendonitis, myositis, neuralgia, synovitis, arthritis, including rheumatoid and osteoarthritis, ankylosing spondylitis, bursitis, colic gastroenteritis, colitis, cystitis, ophthalmitis, burns and injuries, and following surgical and dental procedures. In addition, such a compound may inhibit cellular neoplastic transformations and metastic tumor growth and hence can be used in the treatment of cancer. Polymorph B may also be of use in the treatment and/or prevention of cydooxygenase-mediated proliferative disorders such as may occur in diabetic retinopathy and tumour angiogenesis.

Polymorph B will also inhibit, prostanoid-induced smooth muscle contraction by preventing the synthesis of contractile prostanoids and hence may be of use in the treatment; of premature labor, asthma and eosinophil related disorders. It will also be of use in the treatment of age-related dementia, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), Polymbrph B will prove useful as an alternative to conventional non-steroidal antiinflammatory drugs (NSAID'S) particularly where such non-steroidal anti inflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Polymorph B, will be useful as a partial or complete substitute for conventional NSAID'S in preparations wherein they are presently co-administered with other agents or ingredients.

Thus in further aspects, the invention encompasses pharmaceutical compositions for treating cydooxygenase-2 mediated diseases as defined above comprising a non-toxic therapeutically effective amount of Polymorph B and one or more ingredients such as another pain reliever including acetominophen or phanacetin; a potentiator including acetominvphen or phenacetin; a potentiator including caffeine; an $H_2$-antagonist, aluminum or magnesium hydroxide, simethicone, a decongestant including phenylephrine, phenylpropanolamine, pseudophedrine, oxymetalozine, ephinephrine, naphazoline, xylometazoline, propylhexeddne, or levodesoxyephedrine, an antiitussive including codeine, hydrocodone, caramiphen, carbetapentahe, or dextramethorphan; a prostaglandin including misoprostol, enprostil, rioprostil, omoprostol or rosaprostol; a diuretic; a sedating or non-sedating antihistamine.

In addition the invention encompasses a method of treating cyclooxygenase mediated diseases comprising: administration to a patient in need of such treatment a non-toxic therapeutically effective amount of Polymorph B, optionally co-administered with one or more of such ingredients as listed immediately above.

For the treatment of any of these cyclooxygenase mediated diseases Polymorph B may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily solutions, aqueous or oily suspensions, dispersible powders or granules, emulsions, hard, or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets.

These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubrificating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredients is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occuring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspension s may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsion's may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-aceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Polymorph B may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For oral or topical use, creams, ointments, gels, solutions, pastes, suspensions, etc., containing the compound of 3-(cyclopropylmethoxy)-4-[4-(methylsulfonyl)phenyl]-5,5-dimethyl-5H-furan-2-one are employed. (For purposes of this application, topical application shall include mouth washes and gargles). Topical formulations may generally be comprised of a pharmaceutical carrier, cosolvent, emulsifier, penetration enhancer, preservative system, and emollient.

Dosage levels of the order of from about 0.01 mg to abort 140 mg/kg of body weight per day are useful in the treatment of the above-indicated conditions, or alternatively about 0.5 mg to about 7 g per patient per Day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of animals may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the ago, body weight, general health, sex, diet, time of administration, route of administration, rate of excretion, drug combination and the severity of the particular disease undergoing therapy.

Compounds which inhibit gastric acid secretion in the stomach or act as proton pump inhibitors are well known to the practitioner and are also provided for in the present invention. These compounds include 2-(2-benzimidazolyl-pyridines) and their salts. Such compounds are described, for example in EP 005 129, U.S. Pat. No. 4,255,431 as well as in U.S. Pat. No. 5,629,305. These compounds are also known to treat Helicobacter infections, U.S. Pat. No. 5,093,342, and to act as synergists when combined with an acid degradable antibiotic, see e.g. U.S. Pat. No. 5,629,305. These synergistic combinations may also be formulated in the pastes of the present invention. Omeprazole or its salts is an especially preferred compound.

Macrolide antibiotics are also preferred therapeutic agents. Macrolides as a class include the erythromycin and its derivative as well as other derivatives such as the azalides. Erythromycin (MW 733.94 daltons) is the common name for a macrolide antibiotic produced by the growth of a strain of Streptomyces erythreous. It is a mixture of three erythromycins, A, B and C consisting largely of erythromycin A which is represented by the formula:

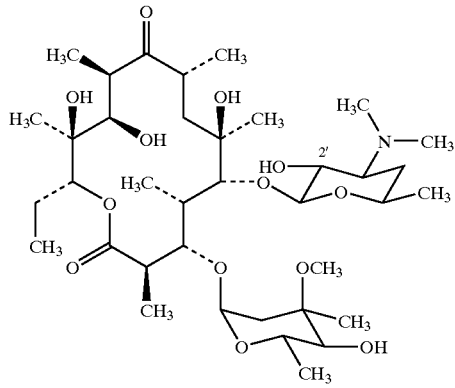

Its chemical name is (3R*,4S*,5S*,6R*,7R*,9R*,11R*, 12R*, 13S*,14R*)-4-[(2,6-dideoxy-3-C-methyl-3-O-methyl-α-L-ribo-hexopyranosyl)-oxy]-14-ethyl-7,12,13-trihydroxy-3,5,7,9,11,13-hexamethyl-6[[3,4,6-trideoxy-3-(dimethylamino)-β-D-xylo-hexapyranosyl]oxy] oxacyclotetradecane-2,10-dione, ($C_{37}H_{67}NO_{13}$).

Erythromycin has a broad and essentially bacteriostatic action against many Gram-positive and some Gram-negative bacteria as well as other organisms including mycoplasmas, spirochetes, chlamydiae and rickettsiae. In humans, it finds usefulness in the treatment of a wide variety of infections. It finds wide application in veterinary practice in the treatment of infectious diseases such as pneumonias, mastitis, metritis, rhinitis, and bronchitis in, for example, cattle, swine and sheep.

Other derivatives of erythromycins include carbomycin, clarithromycin, josamycin, leucomycins, midecamycins, mikamycin, miokamycin, oleandomycin, pristinamycin, rokitamycin, rosaramicin, roxithromycin, spiramycin, tylosin, troleandomycin, and virginiamycin. As with the erythromycins, many of these derivatives exist as component mixtures. For example, carbomycin is a mixture of carbomycin A and carbomycin B. Leucomycin exists as a mixture of components $A_1$, $A_2$, $A_3$, $A_9$, $B_1$–$B_4$, U and V in various proportions. Component $A_3$ is also known as josamycin and leucomycin V is also known as miokomycin. The major components of the midecamycins is midecamycin A and the minor components are midecamycins $A_2$, $A_3$ and $A_4$. Likewise, mikamycin is a mixture of several components, mikamycin A and B. Mikamycin A is also known as virginiamycin $M_1$. Pristinamycin is composed of pristinamycins $I_A$, $I_B$, and $I_C$, which are identical to virginiamycins $B_2$, $B_{13}$ and $B_2$ respectively, and pristinamycin $II_A$ and $II_B$, which are identical to virginiamycin $M_1$ and 26,27-dihydrovirginiamycin $M_1$. Spiramycin consists of three components, spiromycin I, II, and III. Virginiamycin is composed of virginiamycin $S_1$ and virginiamycin $M_1$. All these components may be used in this invention. Sources of these macrolides are well known to the practitioner and are described in the literature in references such as "The Merck Index," 12th ed., S. Budarari, ed., Merck & Co., Inc., Whitehouse Station, N.J. (1996).

Azalides are semisynthetic macrolides antibiotics related to erythromycin A and exhibit similar solubility characteristics. This class includes compounds of the general structure and the pharmaceutically acceptable salts and esters thereof, and the pharmaceutically acceptable metal complexes thereof, wherein $R^1$ is hydrogen;

hydroxy;

$C_{1-4}$ alkoxy;

formyl;

$C_{1-10}$ alkylcarbonyl, $C_{1-10}$ alkoxycarbonyl, aryloxycarbonyl, $C_{1-10}$ aralkoxycarbonyl, $C_{1-10}$ alkylsulfonyl, or arylsulfonyl wherein said $C_{1-10}$ alkyl group or aryl group is unsubstituted or substituted by 1–3 halo (F, Cl, Br), hydroxy, amino, $C_{1-5}$ acylamino or $C_{1-4}$ alkyl groups; or unsubstituted or substituted C01-10 alkyl, $C_{2-10}$ alkenyl or $C_{2-10}$ alkynyl wherein said substituents are independently 1–3 of (a) aryl or heteroaryl optionally substituted by 1–3 halo (F, Cl, Br, I), $C_{1-4}$ alkyl, $C_{1-3}$ alkoxy, amino, $C_{1-4}$ alkylamino, di($C_{1-4}$ alkyl) amino or hydroxy, (b) heterocyclyl optionally substituted by hydroxy, amino, $C_{1-4}$ alkylamino, di($C_{1-4}$ alkyl)amino, $C_{1-4}$ alkylcarbonyloxy or $C_{1-4}$ alkylcarbonylamino, (c) halo (F, Cl, Br or I), (d) hydroxy optionally acylated by a group wherein $R^a$ is hydrogen, $C_{1-6}$ alkyl, aryl, heteroaryl, aralkyl, or heteroaralkyl and $R^b$ is $C_{1-4}$ alkyl or aryl, (e) $C_{1-10}$ alkoxy, (f) aryloxy or heterocaryloxy optionally substituted by 1–3 halo, hydroxy, amino or $C_{1-4}$ alkyl groups, (g) amino or $C_{1-10}$ alkylamino optionally acylated by a group or $R^bSO_2$, wherein $R^a$ and $R^b$ are as defined above, (g) di($C_{1-10}$ alkyl)amino, (h) arylamino, heteroarylamino, aralkylamino or heteroarylakylamino wherein said aryl or heteroaryl group is optionally substituted by 1–3 halo, hydroxy, amino or $C_{1-4}$ alkyl groups, (i) mercapto, (j) $C_{1-10}$ alkylthio, alkylsulfinyl or alkylsulfonyl, arylthio, arylsulfinyl or arylsulfonyl wherein said aryl group is optionally substituted by 1–3 halo, hydroxy, amino or $C_{1-4}$ alkyl groups, (k) formyl, (l) $C_{1-10}$ alkylcarbonyl, (m) alkylcarbonyl, heteroarylcarbonyl, aralkylcarbonyl or heteroarylalkylcarbonyl wherein said aryl or heteroaryl group is optionally substituted by 1–3 halo, hydroxy, amino or $C_{1-4}$ alkyl groups, (n) carboxy, (o) $C_{1-10}$ alkoxycarbonyl, (p) aryloxycarbonyl, heteroaryloxycarbonyl, aralkoxycarbonyl or heterozrylalkoxycarbonyl wherein said aryl or heteroaryl group is optionally substituted by 1–3 halo, hydroxy, amino or $C_{1-4}$ alkyl groups, (q) carbamoyl or sulfamoyl wherein the N-atom is optionally substituted by 1–2$C_{1-6}$ alkyl groups or by a $C_{4-6}$ alkylene chain, (r) cyano, (s) isonitrilo, (t) nitro, (u) azido, (v) iminomethyl optionally substituted on nitrogen or carbon with 0 alkyl, (w) oxo, or (x) thiono;

wherein said alkyl chain, if more than two carbons in length, can be optionally interrupted by 1–2 oxa, thia or aza (—NR-wherein R is hydrogen or $C_{1-3}$ alkyl) groups.

$R^{10}$ is hydrogen or $R^1$ and $R^{10}$ together are $C_1$–$C_3$ alkylene optionally substituted by an oxo group;

$R^1$ and $R^4$ together are $C_1$–$C_3$ alkylene optionally substituted by an oxo group $R^2$ and $R^3$ are hydrogen, $C_{1-10}$ alkyl, aryl $R^2$ and $R^3$ together are oxo and thiono;

$R^4$ and $R^5$ are independently hydrogen and alkylcarbonyl;

$R^4$ and $R^5$ are together carbonyl;

$R^6$ and $R^7$ are both hydrogen or one of $R^6$ and $R^7$ is hydrogen and the other is hydroxy, an acyloxy derivative taken from the group consisting of formyloxy, $C_{1-10}$ alkylcarbonyloxy, arylcarbonyloxy and aralkylcarbonyloxy, or —NHR$^{12}$ wherein R$^{12}$ is hydrogen, arylsulfonyl or heteroarylsulfonyl optionally substituted by 1–3 halo or $C_{1-3}$ alkyl groups, alkylsulfonyl, or

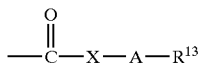

where

X is a connecting bond, O or NH,

A is a connecting bond or $C_1$–$C_3$ alkylene

R$^{13}$ is hydrogen, $C_1$–$C_{10}$ alkyl, aryl, aralkyl, heteroaryl, heterocyclyl, or $C_3$–$C_7$ cycloalkyl, any of which R$^{13}$ groups other than hydrogen can be substituted by one or more of halogen, hydroxyl, $C_1$–$C_3$ alkoxy, cyano, isonitrilo, nitro, amino, mono- or di-($C_1$–$C_3$)alkylamino, mercapto, $C_1$–$C_3$ alkylthio, $C_1$–$C_3$ alkylsulfinyl, $C_1$–$C_3$ alkylsulfonyl, arylthio, arylsulfinyl, sulfamoyl, arylsulfonyl, carboxy, carbamoyl, $C_1$–$C_3$ alkylcarbonyl, or $C_1$–$C_3$ alkoxycarbonyl;

R$^6$ and R$^7$ are together oxo, hydroxyimino, alkoxyimino, aralkoxyimino or aminoimino;

R$^8$ is methyl, aralkoxycarbonyl, and arylsulfonyl;

R$^9$ is hydrogen, formyl, $C_{1-10}$ alkylcarbonyl, $C_{1-10}$ alkoxycarbonyl, and arylalkoxycarbonyl;

m and n are independently integers of zero or one; and said metal complex is taken from the group consisting of copper, zinc, cobalt, nickel and cadmium.

These compounds are disclosed in EP 568 699, herein incorporated by reference. Azalides as a class of components is well-known in the art and further derivatives are described, for example, in U.S. Pat. Nos. 5,869,629; 5,629, 296; 5,434,140; 5,332,807; 5,250,518; 5,215,890; and 5,210,235, all incorporated herein by reference.

Particularly preferred is azithromycin. The structure of azithromycin is

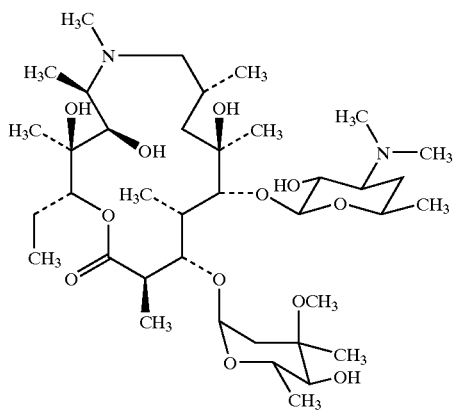

Compounds termed herein formula I and formula II have the following structures:

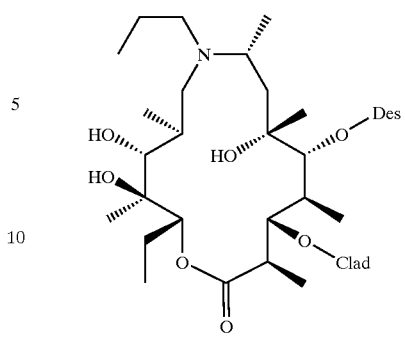

wherein Des is desosomine and Clad is cladinose (formula I) and

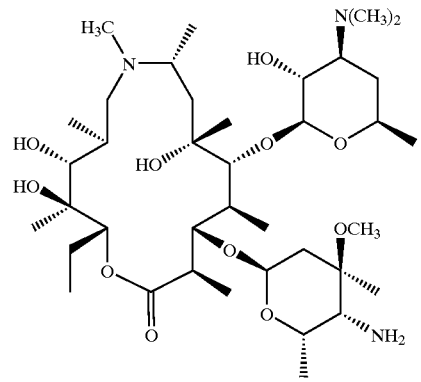

(formula II). The compound of formula II are also known as 8a-azalide. These compounds are disclosed in EP 508 699, herein incorporated by reference. The corresponding basic and acid addition salts and ester derivatives of the macrolides, including the azalides compounds, are also contemplated. These salts are formed from the corresponding organic or inorganic acids or bases. These derivatives include the customary hydrochloride and phosphate salts as well as the acetate, propionate and butyrate esters. These derivatives may have different names. For example, the phosphate salt of oleandomycin is matromycin and the triacetyl derivative is troleandomycin. Rokitamycin is leucomycin V 4-B-butanoate, 3B-propionate.

The term "therapeutic agent" also includes the pharmaceutically or veterinary acceptable acid or base salts, where applicable, of these compounds. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$–$C_{20}$ aliphatic carboxylic acids, which are optionally substituted by halogen or by hydroxyl groups, or $C_6$–$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, steak acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The ester and amide derivatives of these compounds, where applicable, are also contemplated. Specific compounds which belong to these classes of therapeutic agents are well known to the practitioner of this art.

An important feature of the present invention is the combination of a viscosity modifier to the formulation. The addition of the viscosity modifier provides for a paste formulation which contains less fumed silica than the amount normally used in a conventional paste. The inventive formulation allows for all the air that is introduced into the formulation by the fumed silica to escape when the viscosity is low. The viscosity modifier is then added to bring the viscosity of the paste to the desired level without the introduction of more air into the final product. While not wishing to be bound by theory, it is believed that because of their functional groups, the viscosity modifiers act as crosslinkers and extend the three-dimensional network formed by the interaction of the silica and the hydrophobic carrier. The viscosity modifiers also extend the crosslinking density in the formulation.

Especially preferred hydroxy-containing viscosity modifiers include PEG 200, PEG 300, PEG 400, and PEG 600. Other hydroxyl-containing viscosity modifiers include block copolymer mixtures of polyoxyalkylene compounds, i.e., poloxamers including ethylene oxide and propylene oxide poloxamer mixtures, such as those described in U.S. Pat. Nos. 4,343,785; 4,465,663; 4,511,563; and 4,476,107, the disclosures of which are hereby incorporated herein by reference. Commercial versions of these nonionic poloxamer surfactants are available from BASF—Wyandotte Co., Wyandotte, Mich. and include various Pluronics such as Pluronic L81, Pluronic F108, and F127 and those Pluronics described in "Pluronic & Tetronic Surfactants", BASF Corp., 1987, as well as in "The Merck Index", $10^{th}$ ed., on page 1090 and in Remington Pharmaceutical Science. Other suitable density modifiers useful as of the present invention include: polyoxyethylene sorbitan monoleate (Polysorbate 80); polyethylene glycols (Pluracols); nonylphenol ethoxylates (Surfonics); and linear alcohol ethoxylates polyethyleneglycol paraisooctyphenylethers (Tritons's).

Propylene glycol mono- and di-fatty acid esters are also provided for in the inventive formulations. These esters include, for example, propylene glycol dicaprylate; propylene glycol dilaurate, propylene glycol hydroxystearate, propylene glycol isostearate, propylene glycol laurate, propylene glycol ricinoleate, and propylene glycol stearate, most preferably propylene glycol caprylic-capric acid diester as is available under the Trade Name MIGLYOL 840.

Other compounds which function as viscosity modifiers are those which contain both hydroxy and amino function groups. Such compounds include, for example, monoethanolamine, diethanolamine and triethanolamine. These compounds, as well as their use, are well known to a practitioner in the pharmaceutical and veterinary arts.

The amount of viscosity modifier varies from formulation to formulation and the determination of the amount required is well within the routine skill of a practitioner in the formulation art. Preferred is about 0.01 to about 20% of viscosity modifier, based upon total weight of the composition. An especially preferred amount is about 0.05 to about 5%, with about 0.1 to about 2% being most preferred.

Fumed silica is used as the thickening agent. In the pastes according to this invention, the amount of fumed silica is very low. This allows an intermediate with a low viscosity, which in turn allows for a quick escape of the air by buoyancy. After letting the intermediate settle for about 10 minutes, no air was detected in the intermediate. Preferred pastes comprise from about 1 to about 20%, based upon total weight of solution, with from about 1% to about 6% being preferred. Amounts of about 0.02% to about 20%, about 1% to 6.5% or about 1 to about 4% or 5% are also preferred. A paste where the amount of silica is about 4.25% is especially preferred.

The carrier is another important component of the formulation. It is the liquid phase that dissolves the active drug to give an excellent content uniformity and bioavailability. Compounds which act as carriers include solvents that are suitable for pharmaceutical applications, such as triacetin, short to medium chain mono-, di-, or tri-glycerides, glycerin, water, propylene glycol, N-methyl pyrrolidinone, glycerol formal, polyethylene glycol, polyethylene glycol-polypropylene glycol-polyethylene glycol tri-block copolymers, vegetable oil, sesame oil, soybean oil, corn oil, mineral oil, peanut oil, castor oil, cotton oil, transcutol, benzyl alcohol, N,N-dimethylformamide, dimethylsulfoxide, or the like. These compounds may be used alone or as mixtures. Triacetin is especially preferred as it has some water solubility that allows an easy cleaning of the manufacturing equipment. Unlike some aqueous based pastes, triacetin does not support microbial growth, which eliminates the need for a preservative. Mixtures of other carriers with triacetin are also preferred. The amount and type of hydrophobic carrier for a particular formulation is well within the skill level of the practitioner.

When present, any of the conventional pharmaceutical or veterinary colorants may be used. Such colorants include, for example, dyes, aluminum lakes, colorants based upon iron oxide, caramel or combinations of various colorants. Preferably up to about 20%, by weight of total composition, may be present with about 0.001 or 0.01% to about 10% and 0.001 to about 4% being most preferred.

Absorbents may also be added to the paste formulation. Such compounds are well known in the art to the practitioner as well as their use in pastes. These compounds effectively prevents or alleviates the phase separation of the product during storage. Preferred absorbents include magnesium carbonate, calcium carbonate, starch, cellulose and its derivatives, or mixtures of absorbents with magnesium carbonate being especially preferred. The inclusion of these compounds is optional with amounts of 0% to about 30%, 0 to about 15% or about 1% to about 15% or about 1% to about 10%, based on total weight of the composition being especially preferred.

In addition to the therapeutic agent, the viscosity modifier, and the carrier, the formulation can contain other inert ingredients such as antioxidants, preservatives, stabilizers or surfactants. These compounds are well known in the formulation art. Antioxidant such as an alpha tocopheral, ascorbic acid, ascrobyl palmitate, fumeric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation. Preservatives such as the parabens (methylparaben and/or propylparaben) are suitably used in the formulation in amounts ranging from about 0.01 to about 2.0%. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal; and the like.

Surfactants can also be added to help solublize the active drug, to prevent crystallization, and to prevent phase separation. Some examples of the surfactants are: glyceryl monooleate, polyoxyethylene sorbitan fatty acid esters, sorbitan esters, polyvinyl alcohol, Pluronics, sodium lauryl sulfate, etc. Again, these compounds, as well as their amounts are well known in the art.

The instant formulation is equally applicable to other compounds used for pastes as long as such compounds are soluble in the carrier. Additional compounds that can be used in this formulation are other antiparasitic agents and antibiotics, therapeutic vitamin and mineral supplements, and other agents that are assisted in their therapeutic effect by having improved stability over a prolonged period of time. Again, such compounds would be well known to the practitioner.

The pastes are administered to a warm-blooded animals, such as humans, cattle, sheep, pigs, cats, dogs, horses, and the like, by oral, topical, dermal and subdermal administration. The inventive pastes may also be administered to humans. The amount of therapeutic agent depends on the individual therapeutic agent, the animal being treated, the disease state, and the severity of the disease state. The determination of those factors is well within the skill level of the practitioner. Generally, such preparation normally contain about 0.0005 to about 50% of therapeutic agent by total weight of composition. Preferred formulations are those containing about 0.01 to 10% of therapeutic agent and especially preferred formulations are those containing about 2.5 to about 5% of therapeutic agent. Other preferred amounts include about 0.1 to about 0.01 to about 50% or about 10% or about 0.5 to about 3%. For the avermectins and milbemycins, the formulations will generally be prepared to administer from about 0.1 to about 2 mg/kg, preferably from about 0.4 to about 0.85 mg/kg and most preferably from about 0.6 to about 0.7 mg/kg of the active ingredient. At a preferred dose volume of about 1 ml to treat 50 kg of animal body weight the formulation contains from about 5 to about 50 mg of the active agent per ml of solution or about 0.5 to about 10%, preferably about 2.5 to about 5% w/v. However, depending upon the activity of the compound and the animal being treated, doses as low as about 0.3% of the active ingredient are usable. For nodulisporic acid and its derivatives, a formulation containing about 0.0005 to about 5% of the active compound is preferred.

The present invention also provides for a process to prepare paste formulations which is easier and relatively inexpensive. Because fumed silica is a relatively expensive and difficult to handle material, the use of a density modifier reduces the overall cost of the product and minimizes the material handling issue. The manufacturing process is described as follows:

1. In a proper mixer, charge all or a portion of the carrier. Add the active drug and mix it until all of the drug is dissolved.
2. Add the colorant and magnesium carbonate, if necessary. Apply appropriate mixing action to uniformly disperse the titanium dioxide and magnesium carbonate.
3. Add fumed silica to the mixer in a single charge or in portions. Apply appropriate mixing action to uniformly disperse the fumed silica.
4. Add the remaining portion of the triacetin to the mixer. Apply appropriate mixing action to produce a uniform intermediate.
5. Let the intermediate settle for a proper amount of time to let the air that was entrapped with the addition of fumed silica to escape.
6. Add the viscosity modifier and mix until a uniform paste product is produced.

In comparison, with the process to prepare prior paste products, such as EQVALAN paste and GASTROGARD paste, which are manufactured using different formulations and processes, this invention has the following advantage. First, the process is much simpler. A 300 kg batch can be made in less than 2 hours, while 5 hours or more are needed for EQVALAN and GASTROGARD pastes. Second, no heating or cooling is required during the manufacturing of this product, which lowers the equipment demand and cost. Many other paste products require heating and/or cooling. Third, this product is not very shear-sensitive. During manufacturing, over mixing of the inventive pastes, to a certain extent, has little effect on the final consistency of the product. This robustness provides for a forgiving manufacturing process. Many other paste products are shear sensitive and careful manufacturing parameter must be maintained to assure product quality. Fourth, the inventive pastes exhibit little temperature sensitivity. Extended storage under accelerated storage condition showed little physical or chemical change. While many other paste products change the viscosity, and/or dry out, and/or separate significantly when stored under high (e.g. 60° C.)/or low (e.g. −20° C.) temperature conditions.

The inventive paste formulations may be used to treat a number of disease states by administering to the host in need thereof an effective amount of the paste containing the therapeutic agent. The determining of a treatment protocol of a specific indication would be well within the skill level of a practitioner in the pharmaceutical or veterinary arts. Disease states which may be treated by the inventive formulations include, for example, treating inflammation, treating osteoarthritis and rheumatoid arthritis pain or fever, treating or preventing insect or parasitic infestations, treating or preventing bacterial infections; or inhibiting excess acid secretions in the stomach for treating stomach ulcers. The hosts include all animals, e.g. cats, dogs, cattle, sheep, horses, pigs, and humans.

EXAMPLES

A better understanding of the present invention and of its many advantages will be had from the following examples, given by way of illustration.

Example 1

The penetration value of placebo pastes were determined in order to demonstrate the ability of the viscosity modifier to increase the viscosity of the paste at low values of fumed silica. Penetration pastes containing 4% CAB-O-SIL and 0.25% to 2% of a viscosity modifier were prepared in a mixed vehicle (triacetin: miglyol 840). The penetration values of the resulting composition are listed below.

TABLE 1

Penetration value of placebo paste (mm)

| Viscosity modifier | Initial | 10 days at 50° C. | 1 month at 50° C. |
| --- | --- | --- | --- |
| MEA 0.25% | 23.4 | 22.7 | 23.7 |
| MEA 0.5% | 25.2 | 25.8 | 25.3 |
| MEA 1.0% | 24.3 | 22.7 | 21.9 |
| MEA 1.5% | 28.1 | 23.8 | 26.2 |
| TEA 0.5% | 25.6 | 21.9 | 20.7 |

TABLE 1-continued

Penetration value of placebo paste (mm)

| Viscosity modifier | Initial | 10 days at 50° C. | 1 month at 50° C. |
|---|---|---|---|
| Tween 80 1% | 32.0 | 20.5 | 21.2 |
| PEG 300 1% | 33.4 | 26.6 | 26.5 |
| PEG 300 2% | 38.4 | 26.1 | 29.1 |
| Pluronic L81 1% | 43.9 | 27.0 | 27.0 |
| None | Too thin to be tested (>65) | 38.9 | 42.2 |

After two months storage at room temperature, pastes changed to pale yellow when MEA was added. Degree of yellowish: MEA 1.5% > MEA 1.0% > MEA 0.5% > MEA 0.25%. No significant color change in pastes with other additives. Also paste with MEA had an acidic smell, while other pastes did not have.

In the table, MEA is the abbreviation for monoethanolamine and TEA is the abbreviation for triethanolamine. The results demonstrate that the viscosity modifiers have the ability to increase dramatically the viscosity of the placebo paste at low CAB-O-SIL levels. The results in Table 3 also demonstrate that the viscosity of all the pastes increased slightly over time. This result is consistent with the data presented in FIG. 2 which demonstrate that after storage for 6 days at 60° C. the viscosity increased slightly. From this data, one would expect that this increase would stop after a few days.

Example 2

The physical stabilities of three pastes according to the present invention were prepared and placed into a 6.1 ml white syringe. The formulations were as follows:

TABLE 2

Paste formulation containing the COX-2 inhibitor, formula III

| | Formula A | Formula B | Formula C |
|---|---|---|---|
| COX-2-inhibitor[a] | 1.16% | 1.16% | 1.16% |
| CAB-O-SIL | 3.5% | 4.0% | 4.0% |
| PFG 300 | — | 1.0% | 1.0% |
| Monoethanolamine | 0.2% | — | — |
| Titanium Dioxide | — | 2.0% | — |
| Triacetin | QS | QS | QS |

[a]3-(cyclopropylmethoxy)-5,5-dimethyl-4-(4-methylsulfonyl)phenyl)-5H-furan-2-one.

a. Chemical Stability

The chemical stability of these formulations was tested over accelerated storage conditions. The results of these tests are provided below in Table 3.

TABLE 3

Chemical stability of paste formulation containing the COX-2 inhibitor, 3-(cyclopropylmethoxy)-5,5-dimethyl-4-(4-methylsulfonyl)phenyl)-5H-furan-2-one.

| | % of initial after 10 days at 60° C. | % of initial after 4 weeks at 60° C. | % of initial after 4 weeks at 40° C. | % of initial after 4 weeks at 40° C./75% RH |
|---|---|---|---|---|
| Formula A | 99.3% | 101% | | |
| Formula B | 98.3% | 99.4% | 99.0% | 99.0% |
| Formula C | 99.4% | 99.4% | | |

From these data one may conclude that the inventive formulations would be stable for a shelf life of two years.

b. Viscosity

Most semi-solid products change viscosity over storage. A useful product viscosity needs to be maintained throughout the shelf-life of a product to ensure animal acceptance and ease of use. Since the viscosity usually changes more and faster under higher temperature, the viscosity change of Formulation A and B was studied at 60° C. (Table 4).

TABLE 4

Viscosity change of Formulation A and B under accelerated storage conditions.

| | Initial | 1 wk 60° C. | 4 wk 60° C. | 4 wk 40° C. | 4 wk 40° C./75% RH |
|---|---|---|---|---|---|
| Formulation A | 22.8 | 22.9 | 22.9 | | |
| Formulation B | 23.7 | 17.7 | 15.2 | 18.5 | 18.7 |

Formulation A used MEA as the viscosity modifier and showed almost no change in viscosity after even 4 weeks at 60° C. Formulation B used PEG 300 as the viscosity modifier and had a slight increase in viscosity after 4 weeks at 60° C. and this increase is expected to stop after longer storage. The viscosity change under 40° C./75% RH was similar to that of 40° C., indicating that the humidity had no impact on paste viscosity. In contrast to Eqvalan or Gastrogard pastes, where Thixcin R was used as the thickener and their viscosity increased from 20–40 mm to 6 mm after 4 weeks at 60° C., the viscosity increase in these formulations is insignificant.

The viscosity of these pastes at extreme use temperature has not been measured. But based on visual observation, these pastes had good consistency at a wide temperature range.

c. Whipping

Slight phase separation; comparable to that of GASTROGARD, was observed in all three formulations, with Formulation B having slightly less separation.

d. Shrinkage and Discoloration

Discoloration was not seen in pastes except those using MEA as the viscosity modifier. Formulation A (containing 0.20% MEA) changed to slightly yellow but still clear. This slight discoloration is known for MEA and it has no impact on the drug.

No shrinkage occurred to all three formulations.

e. Air Entrapment

No air entrapment was noticed in the pastes.

Example 3

Table 5 lists the concentrations of placebo pastes prepared in order to investigate whipping:

TABLE 5

Placebo Pastes

| Formula D | Formula E | Formula F |
|---|---|---|
| 4% CAB-O-SIL | 4.5% CAB-O-SIL | 5% CAB-O-SIL |
| 1% PEG 300 | 1% PEG 300 | 1% PEG |
| 1% MgCO$_2$ | — | — |
| 94% Triacetin | 94.5% Triacetin | 94% Triacetin |

Whipping (phase separation) in all these pastes was reduced with whipping almost unnoticeable in formula D.

Example 4

The viscosity change of these two pastes under accelerated conditions is shown in Table 6.

TABLE 6

Viscosity change of placebo pastes containing 1% PEG 300 and different amounts of CAB-O-SIL under accelerated storage condition.

| Formulation | CAB-O-SIL content | Initial (mm) | 6 days at 60° C. | 14 days at 60° C. |
|---|---|---|---|---|
| D | 4.0% | 34.2 | 27.4 | — |
| E | 4.5% | 23.9 | 18.4 | 18.8 |
| F | 5.0% | 21.1 | 13.0 | 11.9 |

The paste of Formula F with 5% CAB-O-SIL seemed to be unnecessarily over-thickened. The paste of Formula E with 4.5% CAB-O-SIL was better balanced with respect to viscosity and whipping. Moreover, Formula E seemed to provide the best viscosity over storage.

Example 5

The following paste was prepared according to the process of the present invention.

TABLE 7

Formulation example with a COX-2 inhibitor

| Ingredient | Composition in the specific example |
|---|---|
| COX-2 inhibitor[a] | 0.82% |
| Titanium dioxide | 0.2% |
| Magnesium carbonate | 2% |
| Fumed silica | 4.25% |
| Polyethylene Glycol (PEG) 300 | 0.4% |
| Triacetin | QS |

[a]3-(cyclopropylmethoxy)-5,5-dimethyl-4-(4-methylsulfonyl)-phenyl)-5H-furan-2-one.

A portion of the triacetin was charged into a mixer followed by the addition of the COX-2 inhibitor. The compounds were mixed until all the drug was dissolved. Next, titanium dioxide and magnesium carbonate were added. Mixing continued until the titanium dioxide and magnesium carbonate were uniformly dispersed. Subsequent to this, fumed silica was added to the mixer and mixing occurred until the fumed silica was uniformly dispersed. The remaining portion of the triacetin to the mixer. Mixing occurred until a uniform intermediate was obtained. The intermediate was allowed to settle for 10 minutes until the air that was entrapped with the addition of fumed silica escaped. PEG was added and mixing occurred until a uniform paste product was produced.

Example 6

The following paste was prepared using a process similar to that of Example 5. A uniform paste was obtained.

TABLE 8

Formulation example with a COX-2 inhibitor

| Ingredient | Composition in the specific example |
|---|---|
| COX-2 Inhibitor[a] | 1.64% |
| FD&C Blue #1, aluminum lake | 0.005% |
| Magnesium carbonate | 2% |

TABLE 8-continued

Formulation example with a COX-2 inhibitor

| Ingredient | Composition in the specific example |
|---|---|
| Fumed silica | 4.25% |
| Polyethylene Glycol (PEG) 300 | 0.4% |
| Triacetin | QS |

[a]3-(cyclopropylmethoxy)-5,5-dimethyl-4-(4-methylsulfonyl)phenyl)-5H-furan-2-one.

Example 7

The following paste was prepared using a process similar to that in Example 6. A uniform paste was obtained.

TABLE 9

Formulation example with a COX-2 inhibitor

| Ingredient | Composition in the specific example |
|---|---|
| COX-2 inhibitor[a] | 2.5% |
| Titanium dioxide | 1% |
| Fumed silica | 4% |
| Monoethanolamine | 1.0% |
| Triacetin | 50% |
| Miglyol 840 | QS. |

[a]3-(cyclopropylmethoxy)-5,5-dimethyl-4-(4-methylsulfonyl)phenyl)-5H-furan-2-one.

Example 8

In order to test the robustness of the paste obtained by the inventive process, a placebo paste was prepared by the following process:

1. Charge triacetin. Turn on the mixing screw and chopper until the drug is completely dissolved.
2. Stop mixer, add titanium dioxide and turn on the chopper to disperse.
3. Stop the mixer, add CAB-O-SIL in several portions to the mixer. After each portion is added, turn on the mixer to wet the powder.
4. After all CAB-O-SIL is added, mix until uniform.
5. Stop mixer and wait for 10 minutes to let air escape.
6. Add magnesium carbonate. Add the remaining triacetin and PEG 300 to the mixer. Turn on mixing screw to mix until uniform.

Figure 4:
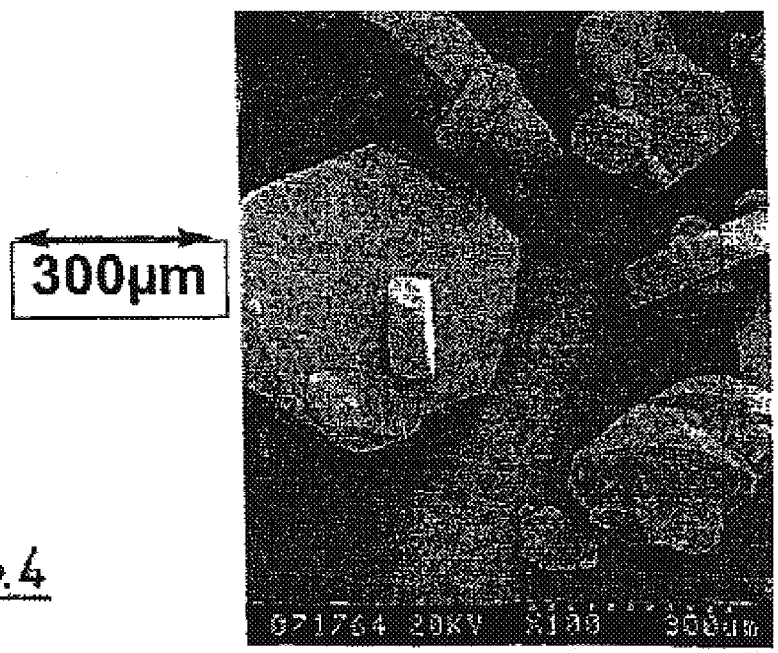
FIG. 4 depicts the sheer sensitivity study of the intermediate product at low sheer.
Figure 5:
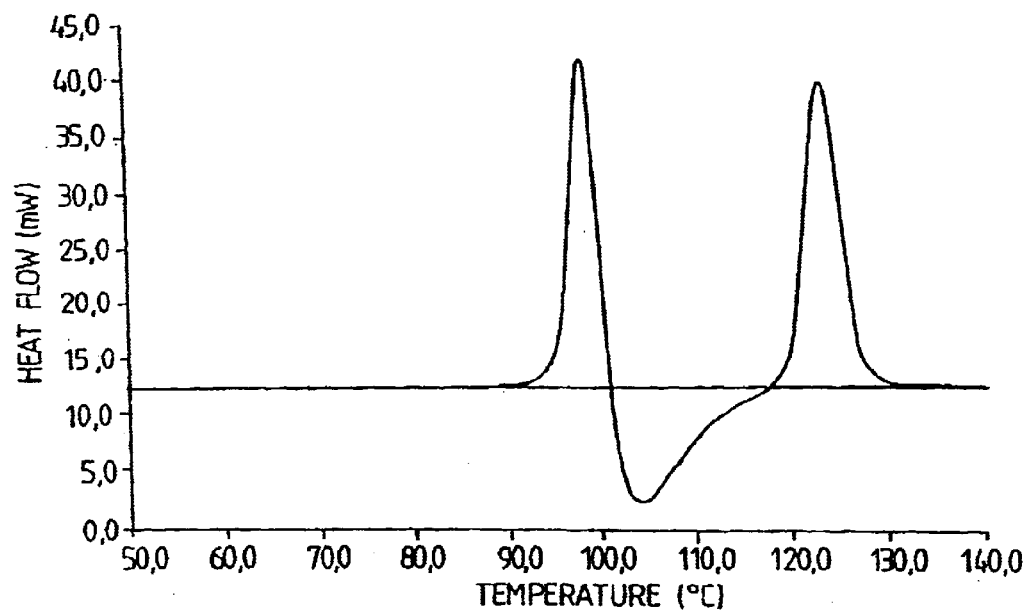
FIG. 5 depicts the sheer sensitivity study of the end product at high sheer.

To determine the robustness of the paste obtained by the inventive process, the intermediate sample (4% CAB-O-SIL in triacetin) at step 5 was tested with Brookfield viscometer (FIG. 4). Its viscosity seems to be not very sensitive to the low shear testing condition. As shown in FIG. 4, the viscosity remained almost constant throughout the course of a 5 minute measuring in the testing container. To evaluate the shear sensitivity of the end product, the final paste at step 6 was subjected to high shear using a homogenizer at 2500 rpm. Samples were collected at different time intervals and tested using Brookfield viscometer and penetrometer (FIG. 5). Both the Brookfield testing and penetrometer testing of the initial end product and the aged end product at 60° C. demonstrated that the paste at step 6 were only a little sensitive to shear. Based on these data, we conclude that over-mixing during production should not have much impact on the paste viscosity.

Example 9

| Material | % | | Amount | |
|---|---|---|---|---|
| Ivermectin | 3.15% | w/w | 17.6 | gm |
| n-propyl gallate | 0.02% | w/w | 0.10 | gm |
| Thixcin R | 1.0% | w/w | 5.0 | gm |
| triacetin | 40.0% | w/w | 200.0 | gm |
| Myvacet 9-45 | qs 100% | w/w | qs to 500.0 | gm |

Triacetin was added to n-propyl gallate and ivermectin in an Erlenmyer flask and mixed until all of the n-propyl gallate dissolved. Myvacet 9–45 was placed in a non-glass beaker in a 50° C. water bath, and mixed at a low speed with a dispersator mixer until the temperature of the content reached 50° C. Thixcin R was then added slowly to the vortex of the mixing Myvacet 9–45. When all the Thixcin R was added, the speed of the mixer was slowly increased to 60 rpm and mixing continued for 20 minutes. The beaker was removed from the water bath and allowed to cool to 30° C. while mixing continued at about 25 rpm. The triacetin solution was added to the Thixcin R/Myvacet 9–45 mixture and the liquids were mixed until uniform.

Example 10

| Material | % | | Amount/2000 L. | |
|---|---|---|---|---|
| Ivermectin | 3.15% | w/w | 63.0 | kg |
| triacetin | 40.0% | v/v | 800.0 | L |
| hydrogenated castor oil | 1.0% | w/w | 20.0 | kg |
| BHT | 0.02 | w/v | 0.4 | kg |
| methylparaben | 0.18% | w/v | 3.6 | kg |
| propylparaben | 0.02% | w/v | 0.4 | kg |
| Myvacet 9-45 | qs 100% | v/v | qs to 1200.0 | L |

Ivermectin, BUT, methyl and propyl paraben were dissolved in 800 L of triacetin, and the solution was sterile filtered into a 2000 L tank equipped with an agitator. Myvacet 9–45 was sterile filtered into a 150 L tank capable of maintaining a batch temperature of 60° C. and equipped with an agitator and with an aseptic addition of sterile powder capability. The gamma sterilized hydrogenated castor oil was dispersed in the Myvacet 9–45, and the dispersion was heated to 50° C., then transferred to the triacetin solution through a microfluidizer. The liquids were mixed until uniform and then aseptically packaged in low density polyethylene containers.

Example 11

The plasma levels of ivermectin administered once subcutaneously at a dose of 630 mcg/kg bodyweight were determined in cattle for two formulations: formulation I contains ivermectin 3.15%, n-propyl gallate 0.02%, Thixcin R 1.5% and triacetin qs to 100%; formulation II has the composition given in Example 10. Ten animals were used for formulation I and six were used for formulation II. Mean plasma levels (ng/ml) are shown in the following Table:

| | Days post dosing | | | | | |
|---|---|---|---|---|---|---|
| Formulation | 3 | 14 | 21 | 28 | 35 | 42 |
| I | 80 | 18 | 10 | 6 | 4 | 2 |
| II | 21 | 25 | 22 | 16 | 13 | 9 |

The mean plasma level for formulation II was greater than 3 ng/ml on day 70.

The 42-day plasma level of formulation I (2 ng/ml) is not sufficient to produce efficacy against Cooperia onocophora and Nematodirus which require an ivermectin plasma level of 3 to 4 ng/ml.

Example 12

To facilitate the manufacture of large scale batches the following process was developed which results in a product that meets the same release specifications as the product manufactured in Example 10. The formula is also the same as used in Example 10. Ivermectin, BHT, methyl and propyl paraben are dissolved a mixture of the triacetin and Myvacet 9–45. The solution is sterile filtered. The gamma sterilized hydrogenated castor is aseptically dispersed in sterile solution using an in-line educator/homogenizer system. Such in-line system can be a Flashblend system. The product is heated and recirculated through the system until the product temperature is from 42 to 50° C. Then the product is aseptically packaged.

Examples for the preparation of Polymorph B are provided hereunder.

The synthesis of Polymorph A of 3-(cyclopropylmethoxy)-4-[4-(methylsulfonyl)phenyl]-5,5-dimethyl-5H-furan-2-one is disclosed in WO 97/14691 (Example 148).

Example 13

Conversion of Polymorph A to Polymorph B by Stirring in Methanol Without Seeding To a 5 ml flask was added 1 g of methanol arid 1.5 g of polymorph A.

Figure 14:
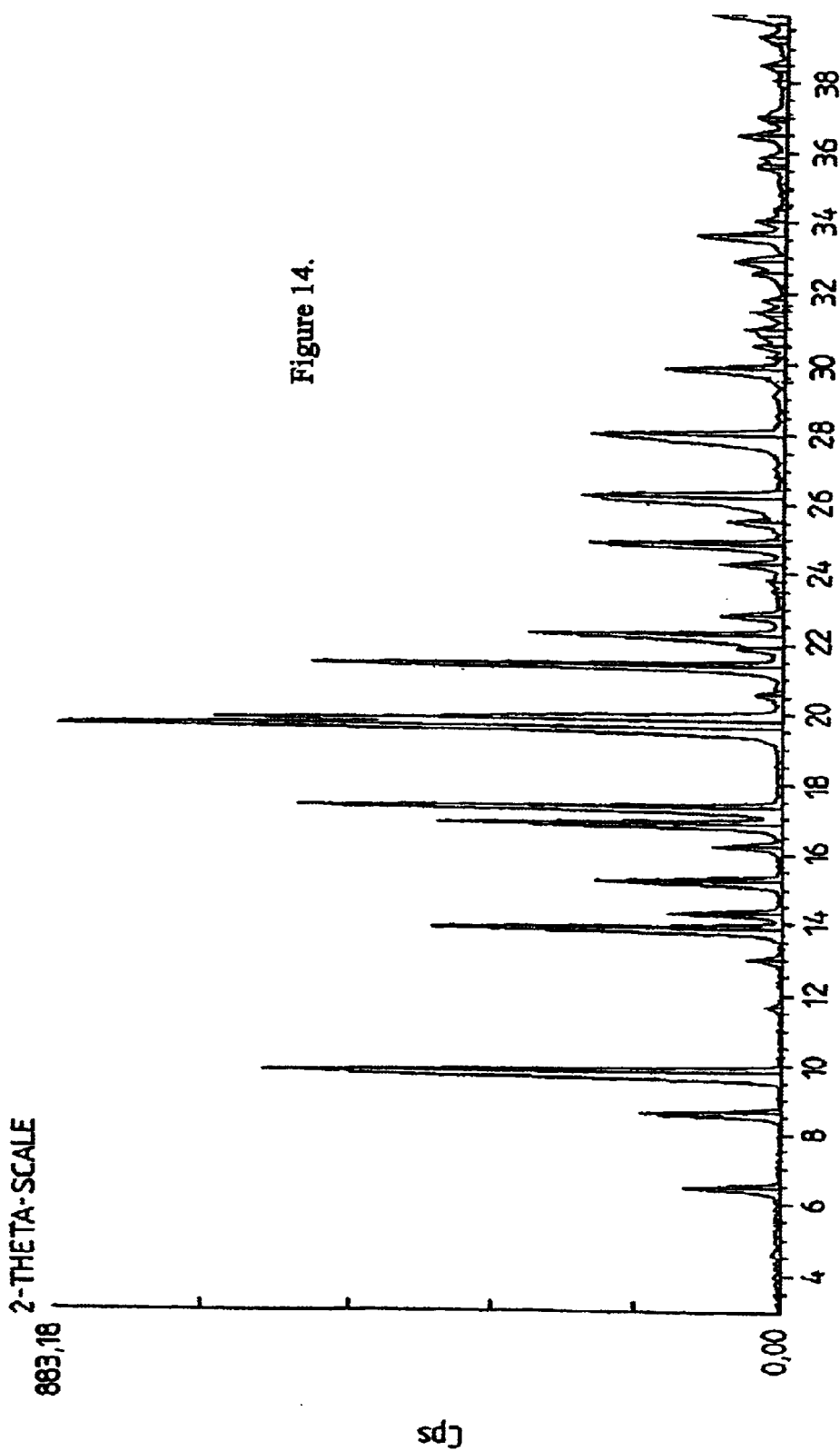
FIG. 14 represents the X-ray diffraction pattern of the end reaction medium used for converting Polymorph A to polymorph B.

The agitation was maintained at room temperature for 50 minutes. All polymorph A had converted to polymorph B after this time. The results on the polymorphic form were confirmed by X-Ray diffraction (FIG. 14)

Example 14

Figure 15:
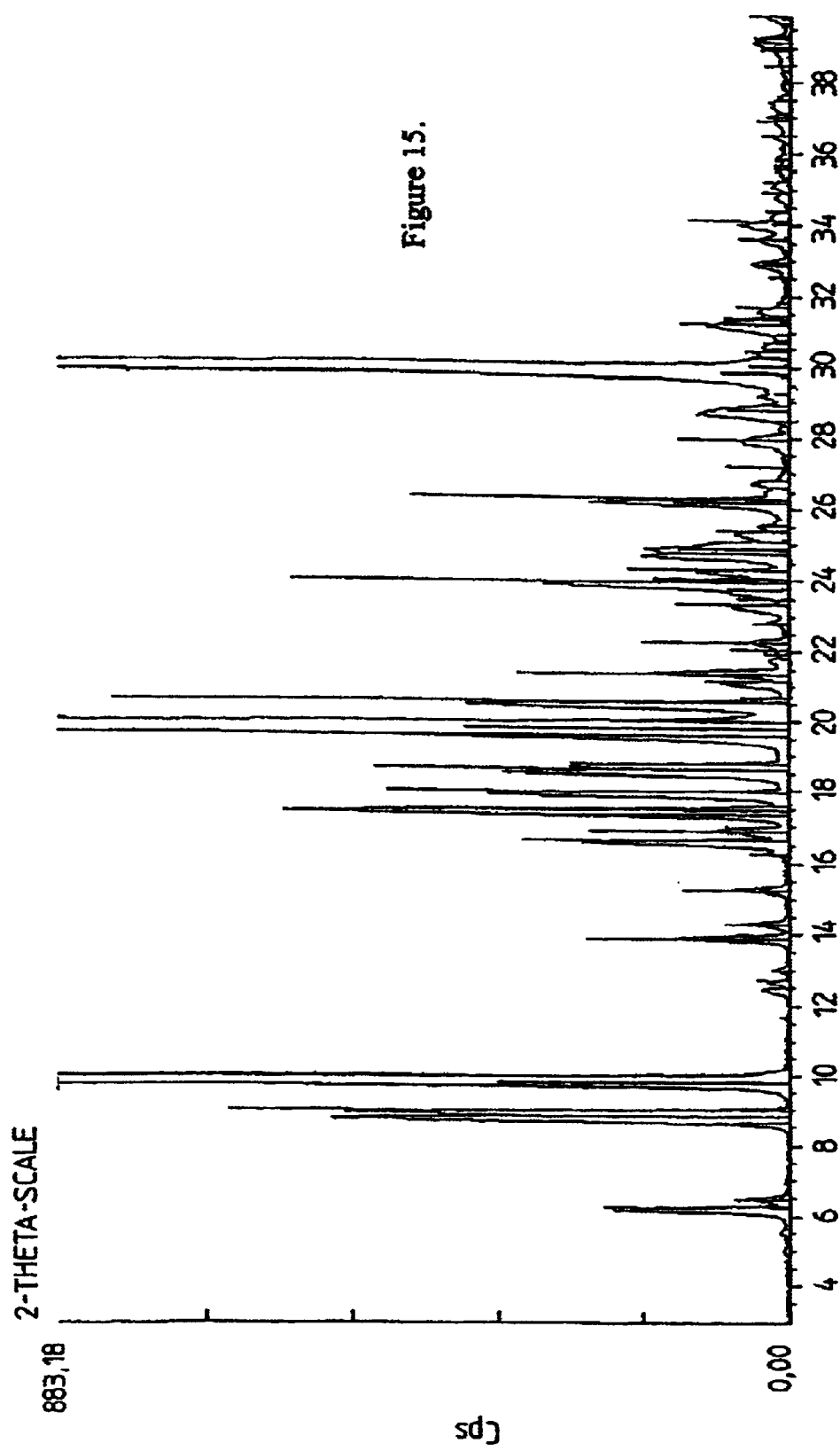
FIG. 15 represents the X-ray diffraction pattern of the initial reaction medium used for converting Polymorph A to polymorph B with seeding.
Figure 16:
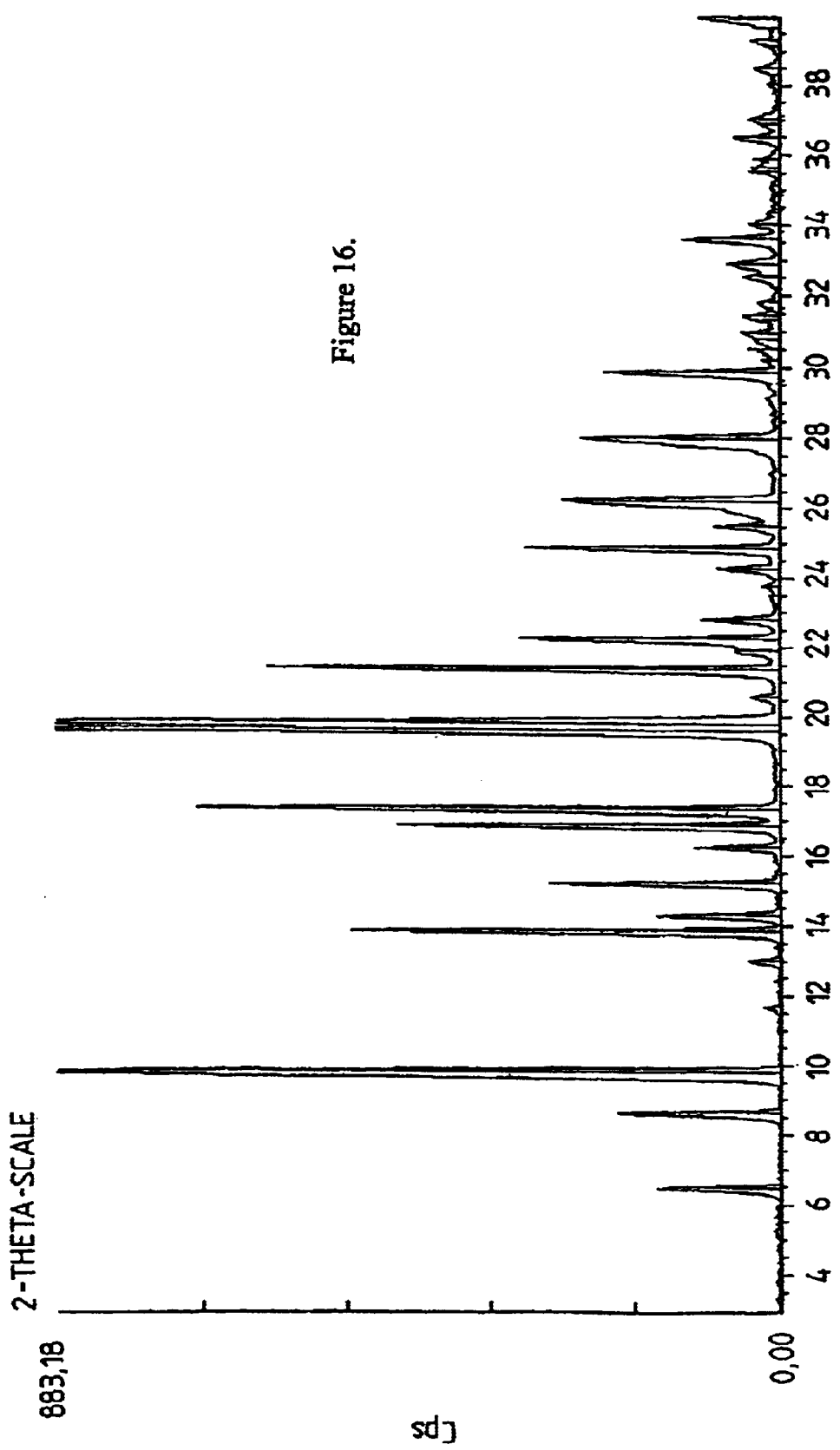
FIG. 16 represents the X-ray diffraction pattern of the end reaction medium used for converting Polymorph A to polymorph B with seeding.

Conversion of Polymorph A to Polymorph B by Stirring in Methanol a 50/50 Mixture of the Two Solids To a 5 ml flask was added 2.85 g of methanol, 0.95 g of polymorph A and 0.95 g of polymorph B The agitation was maintained at room temperature for 50 minutes. All polymorph A had converted to polymorph B after this time. The results on the polymorphic form were confirmed by X-Ray diffraction (FIGS. 15 and 16).

Example 15

Recrystallization of Polymorph A to Polymorph B from a 30% Weight Solution in Methylcyclohexan/Tetrahyfrofuran (30/70 w/w) Seeded with Polymorph B To a 500 ml. flask was added 154 g of polymorph A, 252 g of tetrahydrofuran and 108 g of methylcydohexan. The mixture was heated at 60° C. The batch was in total solution at 58° C.

It was cooled to 48° C. over 10 min. and seeded with polymorph B. Immediate crystallization was observed. The batch was cooled at −13° C. over 30 min., filtered and dried at 70° C. under vacuum.

145.1 g of solid was isolated. The results on the polymorphic form were confirmed by X-Ray diffraction to be polymorph B.

Example 16

Recrystallization of Polymorph A to Polymorph B by Precipitation Process in Methylcyclohexan/ Tetrahyfrofuran (30170 w/w) Seeded with Polymorph B To a 1l flask was added 153 g of polymorph A and 119 g of tetra hydrofuran. The mixture was heated at 50° C. The batch was in total solution at 50° C. The solution is added to a 1 l flask containing 179 g of methylcyclohexan at 0° C. seeded with polymorph B in suspension. Immediate crystallization was observed. During the addition, medium is maintain at 0° C. and aged 60 min. after addition end. The batch is then filtered and dried at 70° C. under vacuum. 144.9 g of dried solid is obtained. The results on the polymorphic form were confirmed by IR analysis to be polymorph B Example 17

One liter of a 20% solution of erythromycin was prepared according to the following procedure:

| Erythromycin (based on a potency of 910 micrograms per milligram) | |
|---|---|
| 200 g/0.910 = | 219.8 g |
| Glacial acetic acid | 16.4 g |
| N-methyl pyrrolidone | 400.0 mL |
| Propylene glycol | qs 1000.0 mL |

The glacial acetic acid was added to a mixture of the N-methyl pyrrolidone and 300 mL of propylene glycol and mixed. The erythromycin was added slowly with stirring. When the erythromycin was completely dissolved, the solution was brought to volume with propylene glycol.

Example 18

Short-term Stability Study

The following 8a-azalide formulation was prepared by placing the dry ingredients into a suitable container, and adding the liquids, while stirring. Stirring was continued until a clear solution was obtained. The composition of the formulation was as follows:

| | |
|---|---|
| 8a-azalide | 12.5% w/v |
| succinic acid | 1.3% w/v |
| sodium bisulfite | 0.5% w/v |
| 40/60% v/v mixture of glycerol formula/ propylene glycol | q.s. AD 100% w/v |

The short-term stability of the formulation was then tested by storing the formulation at 50° C. for eight weeks. No significant changes to the formulation, which remained clear, were observed.

The above description of the invention is intended to be illustrative and not limiting. Various changes or modifications in the embodiment described may occur to those skilled in the art. These can be made without departing from the scope or spirit of the invention.

What is claimed is:

1. A pharmaceutical or veterinary paste formulation comprising:

(a) an effective amount of a Polymorphic B Form of 3-(cyclopropylmethoxy)-4-[4-(methylsulfonyl) phenyl]-5,5-dimethyl-5H-furan-2-one characterized by the following parameters:

| | |
|---|---|
| cristalline system | Trigonal |
| space group | R-3 |
| description | hexagonal |
| unit-cell dimensions | |
| a (Å) | 18.183 |
| b (Å) | 18.183 |
| c (Å) | 26.950 |
| α (°) | 90 |
| β (°) | 90 |
| γ (°) | 120 |
| unit-cell volume (Å$^3$) | 7716.5 |
| number of molecules per unit-cell Z | 18 |
| Temperature of measurement (° K) | 293 |
| calculated specific gravity | 1.303 |
| weight absorption coefficient (cm$^{-1}$) | 2.11 |

(b) a fumed silica;

(c) a viscosity modifier comprised of two or more functional groups for forming hydrogen bonds on the surface of the fumed silica; and (d) a carrier.

2. A pharmaceutical or veterinary paste formulation according to claim 1, wherein the Polymorphic B Form of 3-(cyclopropylmethoxy)-4-[4-(methylsulfonyl)phenyl]-5,5-dimethyl-5H-furan-2-one is further characterized by the following X-ray diffraction data calculated from cystalline structure.

| d(Angs) | Intensity |
|---|---|
| 13,596 | w |
| 10,238 | w |
| 9,092 | s |
| 8,983 | m |
| 7,558 | vw |
| 6,798 | vw |
| 6,39 | m |
| 6,39 | vw |
| 6,194 | vw |
| 5,812 | m |
| 5,812 | w |
| 5,444 | w |
| 5,444 | vw |
| 5,249 | s |
| 5,119 | s |
| 5,1 | vw |
| 4,546 | vw |
| 4,532 | s |
| 4,532 | s |
| 4,492 | m |
| 4,461 | m |
| 4,448 | w |
| 4,311 | vw |
| 4,311 | vw |
| 4,155 | s |
| 4,155 | m |
| 4,056 | vw |
| 4,056 | vw |

-continued

| d(Angs) | Intensity |
| --- | --- |
| 4,027 | vw |
| 4,027 | vw |
| 3,995 | m |
| 3,995 | w |
| 3,895 | w |
| 3,74 | vw |
| 3,665 | vw |
| 3,665 | vw |
| 3,581 | m |
| 3,489 | vw |
| 3,489 | vw |
| 3,459 | vw |
| 3,436 | vw |
| 3,436 | vw |
| 3,413 | w |
| 3,413 | vw |
| 3,399 | vw |
| 3,393 | m |
| 3,393 | vw |
| 3,233 | vw |
| 3,209 | w |
| 3,209 | vw |
| 3,195 | w |
| 3,195 | vw |
| 3,184 | m |
| 3,184 | vw |
| 3,179 | vw |
| 3,128 | vw |
| 3,067 | vw |
| 3,031 | vw |
| 3,001 | vw |
| 3,001 | vw |
| 2,994 | vw |
| 2,958 | vw |
| 2,958 | vw |
| 2,932 | vw |
| 2,906 | vw |
| 2,906 | vw |
| 2,888 | vw |
| 2,853 | vw |
| 2,844 | vw |
| 2,813 | vw |
| 2,768 | vw |
| 2,753 | vw |
| 2,729 | vw |
| 2,729 | vw |
| 2,722 | vw |
| 2,722 | vw |
| 2,719 | vw |
| 2,667 | w |
| 2,667 | vw |
| 2,634 | vw |
| 2,624 | vw |
| 2,608 | vw |
| 2,522 | vw |
| 2,519 | vw |
| 2,519 | vw |
| 2,512 | vw |
| 2,504 | vw |
| 2,504 | vw |
| 2,501 | vw |
| 2,464 | vw |
| 2,464 | vw |
| 2,455 | vw |
| 2,438 | vw |
| 2,428 | vw |
| 2,428 | vw |
| 2,417 | vw |
| 2,364 | vw |
| 2,339 | vw |
| 2,301 | vw |

3. The pharmaceutical or veterinary paste formulation of claim 1 additionally comprising:
   (d) an absorbant;
   (e) a colorant; and
   (f) a carrier selected from the group consisting of a triacetin, a monoglyceride, a diglyceride, and a triglyceride.

4. The pharmaceutical or veterinary paste formulation according to claim 3, wherein the viscosity modifier is selected from the group consisting of PEG 200, PEG 300, PEG 400, PEG 600, monoethanolamine, triethanolamine, glycerol, propylene glycol, polyoxyethylene sorbiton monoleate, and poloxamers; the absorbent is selected from the group consisting of magnesium carbonate, calcium carbonate, starch, and cellulose and its derivatives; and the colorant is selected from the group consisting of titanium dioxide, dye and lake.

5. The pharmaceutical or veterinary paste formulation according to claim 1, which, based upon total weight of formulation, comprises:
   (a) about 0.01 to about 50% of the Polymorphic B Form of 3-(cyclopropylmethoxy)-4-[4-(methylsulfonyl) phenyl]-5,5-dimethyl-5H-furan-2-one;
   (b) about 0.02% to about 20% fumed silica;
   (c) about 0.01% to about 20% of a viscosity modifier comprised of two or more functional groups for forming hydrogen bonds on the surface of the fumed silica;
   (d) 0% to about 30% of an absorbent;
   (e) 0% to about 20% of a colorant; and
   (f) a carrier.

6. The pharmaceutical or veterinary paste formulation according to claim 3, which based upon total weight of the formulation, comprises:
   (a) about 0.01 to about 50% of the Polymorphic B Form of 3-(cyclopropylmethoxyl)-4-[4-(methylsulfonyl) phenyl]-5,5-dimethyl-5H-furan-2-one;
   (b) about 1% to about 6.5% fumed silica;
   (c) about 0.05% to about 5% of a viscosity modifier comprised of two or more functional groups for forming hydrogen bonds on the surface of the fumed silica;
   (d) about 1% to about 10% of an absorbent;
   (e) 0.01% to about 10% of a colorant; and
   (f) a carrier.

7. The pharmaceutical or veterinary paste formulation according to claim 3, wherein the colorant is $TiO_2$, the viscosity modifier is PEG 300, the carrier is triacetin, and the absorbent is magnesium carbonate.

8. The pharmaceutical or veterinary paste formulation according to claim 1, further comprising an absorbent.

9. The pharmaceutical or veterinary paste formulation according to claim 1, further comprising a compound selected from the group consisting of a colorant, a stabilizer, a surfactant and a preservative.

* * * * *